(12) United States Patent
Moine et al.

(10) Patent No.: US 10,064,948 B2
(45) Date of Patent: Sep. 4, 2018

(54) IMPLANTABLE BIO-RESORBABLE POLYMER CHARGED WITH FRAGILE MACROMOLECULES

(75) Inventors: Laurence Moine, Saint Cloud (FR); Alexandre Laurent, Courbevoie (FR); Michel Wassef, Paris (FR); Laurent Bedouet, Paris (FR); Stephanie Louguet, Bordeaux (FR); Valentin Verret, Gentilly (FR); Emeline Servais, Janvry (FR)

(73) Assignees: Occlugel, Jouy en Josas (FR); Centre National de la Recherche Scientifique (CNRS), Paris (FR); Assistance Publique Hopitaux de Paris, Paris (FR); Universite Paris Diderot—Paris 7, Paris (FR)

( * ) Notice: Subject to any disclaimer, the term of this patent is extended or adjusted under 35 U.S.C. 154(b) by 214 days.

(21) Appl. No.: 14/003,528

(22) PCT Filed: Mar. 9, 2012

(86) PCT No.: PCT/EP2012/054178
§ 371 (c)(1),
(2), (4) Date: Sep. 6, 2013

(87) PCT Pub. No.: WO2012/120139
PCT Pub. Date: Sep. 13, 2012

(65) Prior Publication Data
US 2013/0344160 A1 Dec. 26, 2013

Related U.S. Application Data

(60) Provisional application No. 61/450,733, filed on Mar. 9, 2011.

(30) Foreign Application Priority Data

Mar. 9, 2011 (EP) .................................... 11305253

(51) Int. Cl.
| | |
|---|---|
| *A61K 47/34* | (2017.01) |
| *A61K 9/00* | (2006.01) |
| *A61L 27/16* | (2006.01) |
| *A61L 27/54* | (2006.01) |
| *A61L 27/58* | (2006.01) |
| *C08F 290/06* | (2006.01) |
| *A61K 9/16* | (2006.01) |
| *A61K 38/00* | (2006.01) |

(52) U.S. Cl.
CPC ............ *A61K 47/34* (2013.01); *A61K 9/0024* (2013.01); *A61K 9/1635* (2013.01); *A61K 9/1641* (2013.01); *A61K 9/1647* (2013.01); *A61L 27/16* (2013.01); *A61L 27/54* (2013.01); *A61L 27/58* (2013.01); *C08F 290/061* (2013.01); *C08F 290/062* (2013.01); *A61K 38/00* (2013.01); *A61L 2300/252* (2013.01); *A61L 2300/258* (2013.01)

(58) Field of Classification Search
CPC .... A61K 47/34; A61K 9/0024; A61K 9/1635; A61K 9/1641; A61K 9/1647; A61K 38/00; A61L 27/16; A61L 27/54; A61L 27/58; A61L 2300/252; A61L 2300/258; C08F 290/061; C08F 290/062
See application file for complete search history.

(56) References Cited

U.S. PATENT DOCUMENTS

| | | | |
|---|---|---|---|
| 6,028,164 A | 2/2000 | Loomis et al. | |
| 7,807,767 B2* | 10/2010 | Kim ..................... | C08F 220/14 526/222 |
| 2008/0131512 A1 | 6/2008 | Hennink et al. | |
| 2012/0230937 A1 | 9/2012 | Moine et al. | |

FOREIGN PATENT DOCUMENTS

WO        2011029867        3/2011

OTHER PUBLICATIONS

Peppas J Cont. Release 1999 p. 81.*
Peppas J Cont. Release, 1999, 62, p. 81.*
Hongliang Euro. Polymer J, 20005, 41, p. 948.*
Leader et al., Protein therapeutics: a summary and pharmacological classification, Nature Reviews/Drug Discovery, vol. 7, pp. 21-39, dated 2008.
O'Hagan et al., Microparticle-based technologies for vaccines, ScienceDirect, Methods, vol. 40, pp. 10-19, dated 2006.
Dai et al, Microencapsulation peptide and protein drugs delivery system, ScienceDirect, Colloids and Surfaces B, Biointerfaces, vol. 41, pp. 117-120, dated 2005.
Freitas et al., Microencapsulation by solvent extraction/evaporation: reviewing the state of the art of microsphere preparation process technology, Journal of Controlled Release, vol. 102, pp. 313-332, dated 2005.
Raghuvanshi et al., Stabilization of Dichloromethane-Induced Protein Denaturation During Microencapsulation, Pharmaceutical Development and Technology, vol. 3(2), pp. 269-276, dated 1998.

(Continued)

*Primary Examiner* — David J Blanchard
*Assistant Examiner* — Thurman Wheeler
(74) *Attorney, Agent, or Firm* — Banner & Witcoff, Ltd.

(57) ABSTRACT

The present invention relates to a macromolecule-loaded bioresorbable crosslinked polymer wherein the polymer is obtainable from the polymerization of: (i) at least one monomer of formula (I) ($CH_2=CR_1$)CO—K wherein: —K represents O—Z or NH—Z, Z representing $(CR_2R_3)_m$—$CH_3$, $(CH_2-CH_2-O)_m$—H, $(CH_2-CH_2-O)_m$—$CH_3$, $(CH_2)_m$—$NR_4R_5$ with m representing an integer from 1 to 30; —$R_1$, $R_2$, $R_3$, $R_4$ and $R_5$ independently represent H or a C1-C6 alkyl; and (ii) at least one bio-resorbable block copolymer cross-linker, and wherein the macromolecule is chosen in the group consisting of proteins and nucleic acids.

18 Claims, No Drawings

(56) References Cited

OTHER PUBLICATIONS

Ru et al., Visual Evidence of Acidic Environment Within Degrading Poly(lactic-co-glycolic acid) (PLGA) Microspheres, Pharmaceutical Research, vol. 17, No. 1, pp. 100-106, dated 2000.
Li et al., Mapping neutral microclimate pH in PLGA microspheres, ScienceDirect, Journal of Controlled Release, vol. 101, pp. 163-173, dated 2005.
Murty et al., Impurity formation studies with peptide-loaded polymeric microspheres Part I. In vivo evaluation, ScienceDirect, International Journal of Pharmaceutics, vol. 297, pp. 50-61, dated 2005.
Ibrahim et al., Stability of insulin during the erosion of poly(lactic acid) and poly(lactic-co-glycolic acid) microspheres, ScienceDirect, Journal of Controlled Release, vol. 106, pp. 241-252, dated 2005.
Houchin et al., Chemical Degradationof Peptides and Proteins in PLGA: A Review of Reactions and Mechanisms, Journal of Pharmaceutical Sciences, vol. 97, No. 7, pp. 2395-2404, dated 2008.
Uchida et al., Instability of Bovine Insulin in Poly(lactide-co-glycolide) (PLGA) Microspheres, Chem. Pharm. Bull. vol. 44(1), pp. 235-236, dated 1996.
Shao et al., Stabilization of pH-Induced Degradation of Porcine Insulin in Biodegradable Polyester Microspheres, Pharmaceutical Development and Technology, vol. 4(4), pp. 633-642. dated 1999.
Lucke et al., Peptide Acrylation by Poly(alpha-Hydroxy Esters), Pharmaceutical Research, vol. 19, No. 2, pp. 175-181, dated 2002.
Sandor et al., Effect of lecithin and MgCO3 as additives on the enzymatic activity of carbonic anhydrase encapsulated in poly(lactide-co-glycolide) (PLGA) microspheres, Biochimica and Biophysica Acta, vol. 1570, pp. 63-74, dated 2002.
Lee et al., Controlled delivery of heat shock protein using an injectable microsphere/hydrogel combination system for the treatment of myocardial infarction, Journal of Controlled Release, vol. 137, pp. 196-202, dated 2009.
Stenekes et al., The Preparation of Dextran Microspheres in an All-Aqueous System: Effect of the Formulation Parameters on Particle Characteristics, Pharmaceutical Research, vol. 15, No. 4, pp. 557-561 dated 1998.
Hennink et al., Controlled release of proteins from dextran hydrogels, Journal of Controlled Release, vol. 39, pp. 47-55, dated 1996.
Inoue et al., The Therapeutic Effects of Basic Fibroblast Growth Factor Contained in Gelatin Hydrogel Microspheres on Experimental Osteoarthritis in the Rabbit Knee, Arthritis &Rheumatism, vol. 54, No. 1, pp. 264-270, dated 2006.
Scorah et al., Experimental Study of a Tetrafunctional Peroxide Initiator: Bulk Free Radical Polymerization of Butyl Acrylate and Vinyl Acetate, Polymer Bulletin, vol. 57, pp. 157-167, dated 2006.
Loubat et al., Telomerization of acrylic acid with mercaptans: Part 2. Kinetics of the synthesis of star-shaped macromolecules of acrylic acid, Polymer International, vol. 50, pp. 375-380, dated 2001.
Odian, Principles of Polymerization, 4th Edition, J. Wiley, New York, dated 1991.
Tian, et al. Amphiphilic Hyperbranched Polymers Containing Two Types of Beta-Cyclodextrin Segments: Synthesis and Properties, Macromol. Chem. Phys., vol. 210, pp. 2107-2117, dated 2009.

Maciollek et al., New Generation of Polymeric Drugs: Copolymer from NIPAAM and Cyclodextrin Methacrylate Containing Supramolecular-Attached Antitumor Derivative, Macromolecular Chemistry and Physics, vol. 211, pp. 245-249, dated 2010.
Ren et al., Noncovalently Connected Micelles Based on a Beta-Cyclodextrin-Containing Polymer and Adamantane End-Capped Poly(E-caprolactone) via Host-Guest Interactions, Journal of Polymer Science: Part A: Polymer Chemistry, vol. 47, pp. 4267-4278, dated 2009.
Cha et al., Biodegradable Polymer Crosslinker: Independent Control of Stiffness, Toughness, and Hydrogel Degradation Rate, Advanced Functional Materials, vol. 19, 3056-3062, dated 2009.
Van Tomme et al., In situ gelling hydrogels for pharmaceutical and biomedical applications, International Journal of Pharmaceutics, vol. 355, pp. 1-18, dated 2008.
Tokuyama et al., Preparation of poly(N-isopropylacrylamide) hydrogel beads by circulation polymerization, Reactive & Functional Polymers, vol. 70, pp. 967-971, dated 2010.
Tobio, et al., Stealth PLA-PEG Nanoparticles as Protein Carriers for Nasal Administration, Pharmaceutical Research, vol. 15, No. 2, pp. 270-275, dated 1998.
Perez, et al., Poly(lactic acid)-poly(ethylene glycol) nanoparticles as new carriers for the delivery of plasmid DNA, Journal of Controlled Release, vol. 75, pp. 211-224, dated 2001.
Couvreur et al., Nanocapsule Technology: A Review, pp. 1-57, dated 2002.
Bessa et al., Bone morphogenetic proteins in tissue engineering: The road from the laboratory to the clinic, part I (basic concepts), Journal of Tissue Engineering and Regenerative Medicine, vol. 2, pp. 1-13, dated 2008.
Bessa et al., Bone morphogenetic proteins in tissue engineering: the road from laboratory to clinic, part II (BMP delivery), Journal of Tissue Engineering and Regenerative Medicine, vol. 2, pp. 81-96, dated 2008.
Ng, et al., Pegaptanib, a targeted anti-VEGF aptamer for ocular vascular disease, Nature Reviews, vol. 5, pp. 123-132, dated 2006.
Vlckova et al., Pharmaceutical applications of isoelectric focusing on microchip with imaged UV detection, ScienceDirect, Journal of Chromatography A, vol. 1181, pp. 145-152, dated 2008.
Lin et al., Hemocompatibility and cytocompatibility of styrenesulfonate-grafted PDMS-polyurethane-HEMA hydrogel, Colloids and Surfaces B: Biointerfaces, vol. 70, pp. 132-141, dated 2009.
Lei et al., Therapeutic angiogenesis Devising new strategies based on past experiences, Basic Rresearch Cardiol, vol. 99, pp. 121-132, dated 2004.
Tamber et al., Formulation Aspects of Biodegradable Polymeric Microspheres for Antigen Delivery, ScienceDirect, Advanced Drug Delivery Reviews, vol. 57, No. 3, pp. 357-376, dated Jan. 2005.
Sinha et al., Biodegradable Microspheres for Protein Delivery, Journal of Controlled Release, ScienceDirect, vol. 90, No. 3, pp. 261-280, dated 2003.
Saeed et al., One-Pot Controlled Synthesis of Biodegradable and Biocompatible Co-Polymer Micelles, Journal of Materials Chemistry, vol. 19, pp. 4529-4535, dated 2009.
PCT/EP2012/054178, International Search Report, dated May 2, 2012.

\* cited by examiner

IMPLANTABLE BIO-RESORBABLE POLYMER CHARGED WITH FRAGILE MACROMOLECULES

FIELD OF THE INVENTION

The present invention relates to swellable and bio-resorbable cross-linked polymers liable to be implanted in an individual and to deliver macromolecules to the individual with control released.

TECHNICAL BACKGROUND

There is a need, in the field of biomaterial implantation, for resorbable and swellable particles charged with fragile bioactive drugs such as macromolecules. However, only incomplete solutions have been devised thus far.

Macromolecules are new types of molecules having particularly interesting therapeutical uses. Especially the specialized biological activities of these types of drugs provide tremendous advantages over other types of pharmaceutics. Examples of macromolecules are proteins and nucleic acids.

Currently more than 130 proteins are marketed (Leader, 21-39, 2008, Nature Reviews). More and more protein drugs are being employed in clinical trials because of advances in biotechnology allowing mass production of recombinant proteins. They are used to treat patients suffering from numerous diseases: cancer (treatment with monoclonal antibodies and interferons), cardiovascular disease, cystic fibrosis, Gaucher disease (treatment with enzymes and proteins in the blood), diabetes (insulin), anemia (erythropoietin), bone defects (bone morphogenetic proteins) and hemophilia (coagulation factors).

Nucleic acids are also macromolecules with medical applications. These therapeutics include plasmids containing transgenes, oligonucleotides, aptamers, ribozymes, DNAzymes, and small interfering RNAs. These drugs can be used to mitigate disease either prophylactically or at a very early stage, preventing disease progression and its complications This type of molecules is very fragile and contact with organic solvent, use of high temperature, shear stress or acidic environment should be avoided. Therefore delivery of macromolecules in the body is a challenge.

Indeed, due to their nature, macromolecules cannot be administered orally. These products tend to degrade rapidly in the gastrointestinal tract, in particular because of the acidic environment and the presence of enzymes therein. Furthermore macromolecules have short in vivo lives.

Moreover, to a higher extent macromolecules are not able to pass endothelial, epithelial and intestinal barriers, due to their size and, generally, polar character.

For these reasons, macromolecules have to be brought in the system parenterally, i.e. by injection. The pharmacokinetic profile of these products is, however, such that injection of the product requires a frequent administration. Sometimes even multiple daily injections or continuous infusions are required for the protein drug to have a desired therapeutic effect. It will be evident that this is inconvenient for patients requiring these drugs. Furthermore, this type of application often requires hospitalization and/or medical supervision and has logistic drawbacks.

In addition, it appears that at least for certain classes of pharmaceutical macromolecules, such as cytokines which are presently used in e.g. cancer treatments, the therapeutic efficacy is strongly dependent on effective delivery on the site where it is needed. In such cases, the macromolecules should be directed to the sites where their activity is needed during a prolonged period of time.

Hence, there is a need for delivery systems which have the capacity for controlled release. In the art, delivery systems consisting of polymeric networks in which the macromolecules such as proteins are loaded and from which they are gradually released have been proposed.

The local delivery of macromolecules is challenging. The main drawback of this approach is the requirement of a polymer solubilization step using a solvent, such as methylene chloride or isopropanol, high temperature, foaming, which can compromise macromolecule stability. Local delivery of nucleic acid into microparticles has several limitations, similar to proteins. These problems include damage to DNA during microencapsulation, low encapsulation efficacy and minimal initial release of entrapped compound (O'Hagan, 10-19, 2006, *Methods*).

One of the most important differences affecting delivery and biological effectiveness of macromolecules in particular protein is complexity of protein structure, close relation between protein efficacy and molecular three-dimensional structure. It is essential to maintain the structural integrity through all the formulations steps of local drug delivery system. The method of encapsulation of proteins in a system of delivery is a critical step that can lead to inactivation of the protein (Sinha and Trehan, 261-280, 2003, *Journal of Controlled Release*). The most commonly used methods for protein drug encapsulation in polymeric microparticles include solvent extraction or evaporation from a W1/O/W2 dispersion, coacervation, and spray drying (Dai, 117-120, 2005, *Colloids and Surface B, Freitas*, 313-332, 2005, *Journal of Controlled Release*; Sinha and Trehan, 261-280, 2003, *Journal of Controlled Release*; Tamber, 357-376, 2005, *Advanced Drug Delivery Reviews*). Many disadvantages are associated with these methods which could cause protein denaturation and instability during encapsulation and release process. Double emulsion method has the limitations of exposure to organic solvents, high shear stress, and aqueous organic interfaces. Spray drying operates at elevated temperature and is not advisable to be used for highly temperature sensitive compounds such therapeutic proteins and nucleic acids.

Briefly, proteins have four levels of structural organization: the primary structure of the linear chain of amino acids along the polypeptide chain, the secondary structure formed by the local folding of the amino acids in a region of polypeptide chain in helices or sheets, the tertiary structure made of a stable arrangement in space of the helices and sheets. The quaternary structure is an arrangement of subunits of these proteins, the active protein consists of several subunits, such as hemoglobin or antibodies (assembly of four protein chains by disulfide bridges established between 2 cysteines). The tertiary or quaternary structure of proteins depends on weak bonds (hydrogen, hydrophobic, ionic) established between amino acid residues of polypeptide chains. These non-covalent bonds are fragile and can be broken under certain conditions leading to protein unfolding. The biological function of a protein depends of its structure, denatured protein can no longer perform its function. The main factors causing protein denaturation are the heat that breaks the weak hydrogen bonds, the pH (too acidic or too alkaline) and the ionic strength. A protein unfolding also occurs in presence of organic solvent, where the hydrophobic regions of folded proteins are turning to outside while the hydrophilic regions will gather in the center of the molecule. During the preparation of microspheres, the proteins can be exposed to both high temperature and organic solvents such as dichloromethane (solvent of PLGA) and be denatured (Raghuvanshi, 269-276, 1998, *Pharm Dev Technol*).

More in detail, at present, two major types of polymeric delivery systems can be distinguished: biodegradable polymers and non-biodegradable hydrogels.

Biodegradable polymers, e.g. polylactic acid (PLA) and copolymers of PLA with glycolic acid (PLGA), are frequently used as delivery systems for macromolecules such as proteins.

Macromolecules can be incorporated in pharmaceutical delivery systems, e.g. microspheres, by a variety of processes. In vitro and in vivo, usually a biphasic release profile is observed: an initial burst followed by a more gradual release. The burst is caused by macromolecules present at or near the surface of the microspheres and by macromolecules present in pores. The gradual release is ascribed to a combination of diffusion of the macromolecules through the matrix and degradation of the matrix. Especially for larger macromolecules diffusion in these matrices is negligible, so that the release depends on the degradation of the polymer. The degradation can be influenced by the (co)polymer composition. A well-known strategy to increase the degradation rate of PLA is co-polymerization with glycolic acid.

Although delivery systems based on biodegradable polymers are interesting, it is very difficult to control the release of the incorporated macromolecule. This hampers the applicability of these systems, especially for macromolecules with a narrow therapeutic window, such as cytokines and hormones. Furthermore, organic solvents have to be used for the encapsulation of the macromolecules in these polymeric systems. Exposure of macromolecules to organic solvents generally leads to denaturation, which will affect the biological activity of the macromolecules. Furthermore, the very stringent requirements of registration authorities with respect to possible traces of harmful substances may prohibit the use of such formulations of therapeutic drugs in human patients.

Moreover PLGA hydrolysis in the core of microspheres causes a local acidification. The pH was measured using pH-sensitive organic probes and values between 1.5-3 were obtained (Fu, 100-106, 2000, *Pharmaceutical Research*; Li and Schwendeman, 163-173, 2005, *Journal of Controlled Release*). The pH drop within polymer matrix of microspheres can induced different alterations of proteins encapsulated in PLGA matrix. The more documented adverse reactions affecting encapsulated proteins are deamidation, acylation and hydrolysis of the peptide bond (Murty, 50-61, 2005, *International Journal of Pharmaceutics*; Abbas Ibrahim, 241-252, 2005, *Journal of Controlled Release*, Houchin and Topp, 2395-2404, 2008, *Journal of Pharmaceutical Sciences*). The deamidation of proteins is an acid-catalyzed reaction in which the amino acids asparagine and glutamine are degraded to aspartic acid and glutamic acid. A significant deamidation was observed for encapsulated insulin (Uchida, 234-236, 1996, *Chem Pharm Bull*, Shao and Bailey, 623-632, 1999, *Pharm Dev Technol*). Acylation is another alteration of proteins entrapped within PLGA microspheres. During microspheres resorption, the proteins can be acylated with glycolic acid or lactic acid adducts. This side reaction was observed in vivo for the Octreotide peptide subcutaneously implanted in PLGA microparticles (Murty, 50-61, 2005, *International Journal of Pharmaceutics*) and in vitro for salmon calcitonin (Lucke, 175-181, 2002, *Pharmaceutical Research*). Acylation occurs on several amino acids: free amine of N-terminal amino-acid of protein, lysine, tyrosine or serine located along the peptide chain.

The local acidity within the microspheres can cause hydrolysis of the peptide chain, particularly at the level of aspartic acid, the Asp-Pro bond is considered fragile. During in vitro release experiment, more than 50% of carbonic anhydrase released after one week from PLGA microspheres (1-3 microns) corresponding to fragments (Sandor, 63-74, 2002, *Biochimica and Biophysica Acta*).

Loaded PLGA microspheres were themselves loaded onto an alginate hydrogel to control the release for prolonged time periods (Lee, Journal of Controlled Release 137, 196-202, 2009). The bioactive compound is still incorporated in PLGA microsphere which may denature its structure during degradation.

Also hydrogels are frequently used as delivery systems for proteins and peptides. Hydrogels can be obtained by crosslinking a water-soluble polymer yielding a three-dimensional network which can contain large amounts of water. Proteins can be loaded into the gel by adding the protein to the polymer before the crosslinking reaction is carried out or by soaking a preformed hydrogel in a protein solution. So, no (aggressive) organic solvents have to be used to load the hydrogels with protein molecules.

In contrast to the biodegradable polymers, the release of proteins from hydrogels can be easily controlled and manipulated by varying the hydrogel characteristics, such as the water content and the crosslink density of the gel. However, a major disadvantage of the currently used hydrogel delivery systems is that they are not biodegradable. This necessitates surgical removal of the gel from the patient after the release of the protein in order to prevent complications of inclusion of the empty hydrogel material (wound tissue is frequently formed).

Biodegradable hydrogels have been used in the preparation of delivery systems for protein drugs. One of these systems comprises crosslinked dextrans obtained by coupling glycidyl methacrylate (GMA) to dextran, followed by radical polymerization of an aqueous solution of GMA-derivatizad dextran (dex-GMA) (Hennink, Pharmaceutical Research, vol 15, no 4, 1998). But size of the microspheres obtained is quite small (around 100 μm).

Proteins can be encapsulated in the hydrogels by adding proteins to a solution of GMA-derivatized dextran prior to the crosslinking reaction. It appeared that the release of the proteins out of these hydrogels depends on and can be controlled by the degree of crosslinking and the water content of the gel (Hennink et al., *J. Contr. Rel.* 39, (1996), 47-57).

Although the described cross-linked dextran hydrogels were expected to be biodegradable, these hydrogels are rather stable under physiological conditions.

To solve this problem US2008/131512 proposes to add a synthetic resorbable polymer (PLA or PGA) between dextran and the methacrylic double bond to facilitate the degradation of the network by hydrolysis. However, due to its chemical nature, dextran is quite difficult to modify in order to introduce specific functional groups onto the structure. These functional groups may help to favour the incorporation of the macromolecules and/or to control the release.

Microspheres can be made with natural polymer (gelatine or collagen). However, the release is rapid (in one week after implantation in rabbit joint cavity) (Inoue, 264-270, 2006, Arthritis & Rheumatism) and precluding their used for long-term and controlled drug delivery. It should also be noted that collagen is of bovine origin and allergic reactions to the bovine proteins are noted in about 2% of patients.

It is therefore a goal of the present invention to solve the above problems, in particular to avoid the macromolecule, such as protein, instability during microspheres preparation, the nonspecific interactions with the polymers, local acidity within the degrading polymer matrix and to obtain a better predictability and control of release of the microsphere with a limited burst effect.

SUMMARY OF THE INVENTION

The present invention arises from the unexpected finding, by the inventors, that the presence of neutral (meth)acrylates in a polymer cross-linked by bio-resorbable PLGA-, PEG- and/or PLA-based block copolymers can influence the rate of degradation of such a polymer while also allowing to control the swelling of the polymer. Furthermore, this type of polymer is particularly suitable for delivering macromolecules to its site of action in the body. Indeed it is possible to use a process for loading the polymer with the macromolecules which preserves the fragile conformation and therefore the activity of macromolecules. In addition, where the polymer is provided as a spherical particle, sphericity can be maintained even upon swelling. This type of polymer is described in patent application No. PCT/EP 2010/063227. It is particularly interesting since it provides a controlled release of the loaded macromolecules. At the opposite of pure PLGA device, the polymer network according to the present invention is not only composed of PLGA but also possesses PEG and methacrylate chains. During degradation of the network, the acidic degradation products of PLGA will be diluted inside the hydrogel and may diffuse out of the structure.

Besides, it was also evidenced by the Applicant that in animal experiments performed in sheep shoulder joints, unlike microspheres of the prior art, polymer of the invention-based microspheres were quickly incorporated into the synovial tissue and that their residency time in synovium was at least of several weeks (1 month), making the microspheres of the invention suitable for delivering drug in the synovium for several weeks or months.

The present invention thus relates to a macromolecule-loaded bioresorbable crosslinked polymer. The polymer is the one described in the patent application No. PCT/EP 2010/063227.

Therefore this polymer is obtainable from the polymerization of:
(i) at least one monomer of formula (I)

$$(CH_2\!=\!CR_1)CO\!-\!K \qquad (I)$$

wherein:
K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
$R_1$, $R_2$, $R_3$, $R_4$ and $R_5$ independently represent H or a $C_1$-$C_6$ alkyl; and
(ii) at least one bio-resorbable block copolymer cross-linker.

Advantageously according to the invention, the above-defined polymer is obtainable from the polymerization of the at least one monomer of formula (I), the at least one bio-resorbable block copolymer cross-linker, and (iii) further at least one chain transfer agent.

Oftentimes, the active species used to initiate polymerization are highly reactive and may conduct in some cases to undesirable side reactions such as chain transfer. This can lead to the production of short or long branches or even more problematically to the formation of non resorbable cross-linking (Scorah 2006, Polym. Bull. 57, 157-167). These structural changes can have adverse effects on the biocompatibility of the material. To avoid these side reactions, appropriate levels of chain transfer agents may be added to the monomer solution without affecting the network formation. These molecules with high transfer reactivity, also called "regulators", are very efficient even at small concentrations. Furthermore the use of at least one transfer agent is an additional way to reduce/control the molecular weight of the polymer chain residue (Loubat 2001, Polym. Int. 50, 375-380; Odian, G. "Principles of polymerization" $3^{rd}$ ed., J. Wiley, New York 1991).

Advantageously, the at least one chain transfer agent is selected from the group consisting of monofunctional or polyfunctional thiols, alkyl halides, transition metal salts or complexes and other compounds known to be active in free radical chain transfer processes such as 2,4-diphenyl-4-methyl-1-pentene.

Particularly advantageously, the at least one chain transfer agent is a cycloaliphatic or preferably aliphatic thiol, typically having from 2 to about 24 carbon atoms, and having or not a further functional group selected from amino, hydroxy and carboxy.

Examples of particularly preferred chain transfer agents are thioglycolic acid, 2-mercaptobutanol, dodecane thiol and hexane thiol.

According to the invention, the at least one chain transfer agent may be present in the reaction mixture in an amount of, for example, from 0.1 to 10%, preferably from 1 to 4%, and in particular from 1.5 to 3.5% by mole, relative to the number of moles of monofunctional monomers.

Advantageously according to the invention, the above-defined polymer is obtainable from the polymerization of the at least one monomer of formula (I), the at least one bio-resorbable block copolymer cross-linker, (iii) optionally at least one chain transfer agent as defined above, and (iv) further at least one cyclic monomer having an exo-methylene group of formula (III):

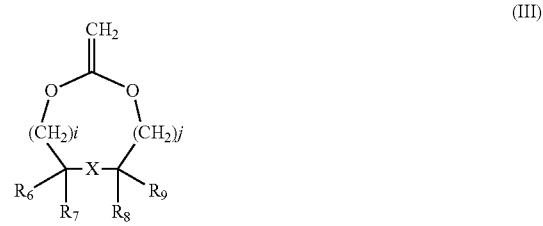

wherein:
R6, R7, R8 and R9 represent independently H or a $C_5$-$C_7$ aryl group or R6 and R9 are absent and R7 and R8 form together with the carbon atom on which they are bonded a $C_5$-$C_7$ aryl group;
i and j represent independently an integer chosen between 0 and 2, advantageously i and j are chosen between 0 and 1, more advantageously i=j, still more advantageously, i=j=1; and
X represents either O or X is not present and in this latter case, $CR_6R_7$ and $CR_8R_9$ are linked via a single bond C—C.

Advantageously, presence of a cyclic monomer having an exo-methylene group during the polymerization of the polymer described in patent No. PCT/EP 2010/063227, can lower the molecular weight of the residue obtained after degradation of the polymer without modifying the mechanical properties of the polymer.

The use of this kind of monomer during the polymerization will increase the number of labile points into the main chain of the polymer network and therefore lower the molecular weight of the residue obtained after hydrolytic degradation. This feature will therefore avoid the unwanted accumulation of polymers in kidneys Indeed, the introduction of ester linkage in the polymer network by the use of cyclic monomer having an exo-methylene group will provide a greater flexibility on the control of degradation of the polymer network.

Preferably according to the invention, the cyclic monomer having an exo-methylene group of formula (III) is selected from the group consisting of 2-methylene-1,3-dioxolane, 2-methylene-1,3-dioxane, 2-methylene-1,3-dioxepane, 2-methylene-1,3,6-Trioxocane, and derivatives thereof, in particular benzo derivatives and phenyl substituted derivatives, advantageously from the group consisting of 2-methylene-1,3-dioxolane, 2-methylene-1,3-dioxane, 2-methylene-1,3-dioxepane, 2-methylene-4-phenyl-1,3-dioxolane, 2-methylene-1,3,6-trioxocane and 5,6-benzo-2-methylene-1,3dioxepane, more advantageously from the group consisting of 2-methylene-1,3-dioxepane, 5,6-benzo-2-methylene-1,3dioxepane, 2-methylene-1,3,6-trioxocane and 2-methylene-1,3,6-trioxocane.

Advantageously, the polymer according to the present invention is obtained by using between 0.1 and 50 mol %, more advantageously between 0.1 and 20 mol %, typically between 1 and 10 mol %, of the above-mentioned cyclic monomer based on the total amount of the monomer.

In an embodiment of the invention, the above-defined polymer is obtainable from the polymerization of the at least one monomer, the at least one bio-resorbable block copolymer cross-linker, optionally at least one chain transfer agent as defined above, optionally at least one cyclic monomer having an exo-methylene group as defined above and at least one further monomer which is a charged, ionisable, hydrophilic, or hydrophobic monomer of the following formula (V):

$(CH_2=CR_{11})CO-M-F$     (V)

wherein:
$R_{11}$ represents H or a $C_1$-$C_6$ alkyl;
M represents a single bond or a linker moiety having from 1 to 20 carbon atoms;
F represents a charged, ionisable, hydrophilic, or hydrophobic group having 100 atoms at the most.

These embodiments are advantageous in that where the polymer of the invention is polymerized from a charged, ionisable, hydrophilic, or hydrophobic monomer as defined above, the polymer may present with various physico-chemical surface characteristics enabling loading, i.e. non-covalently adsorbing, macromolecules to be delivered.

The macromolecule which is loaded in the polymer according to the present invention is chosen in the group consisting of proteins and nucleic acids.

The present invention also relates to at least one polymer as defined above for use as a medicinal product.

The present invention also relates to a pharmaceutical composition comprising at least one polymer as defined above, in association with a pharmaceutically acceptable carrier.

The present invention also relates to at least one polymer as defined above for use as a medicinal product advantageously intended for the correction of skin ageing and/or for wound healing and/or for tissular reconstruction and/or for soft tissue repair, and/or for the treatment of inflammation, benign and malignant tumors, arteriovenous malformations, gastrointestinal bleeding, epistaxis, primary post-partum haemorrhage and/or surgical haemorrhage and/or for regenerating tissue in an human or an animal, or tissue engineering in cell culture.

The present invention also relates to a pharmaceutical composition comprising at least one polymer as defined above, in association with a pharmaceutically acceptable carrier, advantageously intended for administration by injection.

In particular it relates to an injectable pharmaceutical composition comprising
(a) a polymer as described above having a spherical shape of a diameter of between 50 and 500 μm and a resorption time of between a 2 days to 3 weeks;
(b) a polymer as described above having a spherical shape of a diameter of between 50 and 500 μm and a resorption time of between one to 3 months; and
(c) at least one pharmaceutically acceptable excipients, wherein at least one of the polymer (a) or (b) is loaded with a macromolecule as described above.

Advantageously, in the composition according to the present invention, the spherical particles of polymer (a) and (b) do not have the same diameter, advantageously the diameter of the spherical particles of polymer (a) is of between 100 and 300 μm and the diameter of the spherical particles of polymer (b) is of between 300 and 500 μm.

The present invention also relates to an implant containing at least one polymer as defined above or the composition as defined above.

DETAILED DESCRIPTION OF THE INVENTION

Bio-Resorbable Block Copolymer

As intended herein, the expression "bio-resorbable" means that the block copolymer is degraded or cleaved when administered into a living organism, preferably a mammal, in particular a human, organism. As intended herein "bio-resorbable" indicates that the block copolymer may be hydrolyzed.

As intended therein, the expression "copolymer cross-linker" is intended to mean that the copolymer contains a functional group at at least two of its extremities in order to link together several polymer chains. Advantageously this functional group contains a double bond.

Preferably, the bio-resorbable block copolymer cross-linker as defined above is linear and advantageously presents $(CH_2=(CR_6))$— groups at both its extremities, wherein $R_6$ independently represents H or a $C_1$-$C_6$ alkyl. Preferably also, the bio-resorbable block copolymer cross-linker is a diblock or a triblock copolymer.

Block copolymer crosslinker are more advantageous than statistic copolymers since, in particular if one of the block contains PEG, they have the tendency to attract more water molecules and therefore to be more easily hydrolysable. Furthermore, it is easy to change the size of the block and hence to adapt the rate of biodegradability of polymer according to the present invention in function of its intended use.

It is also preferred that the block of the bio-resorbable block copolymer cross-linker as defined above is selected from the groups consisting of polyethylene glycol (PEG), poly-lactic acid (also named poly-lactide) (PLA), poly-glycolic acid (also named poly-glycolide) (PGA), poly-lactic-glycolic acid (PLGA) and poly(caprolactone) (PCL).

As is well known to one of skill in the art, PEG, PLA, PGA and PCL may be represented as follows, n representing their degree of polymerization:

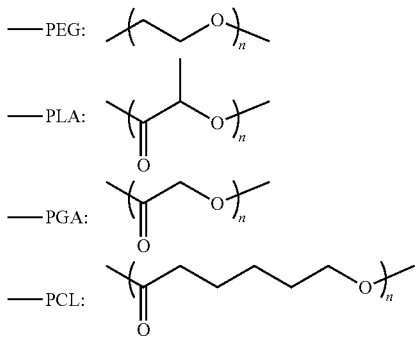

For PLGA which comprises both lactide and glycolide units, the degree of polymerizaton is the sum of the number of lactide and glycolide units.

More preferably, the bio-resorbable block copolymer cross-linker as defined above is of the following formula (II):

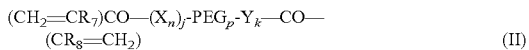

wherein:
$R_7$ and $R_8$ independently represent H or a $C_1$-$C_6$ alkyl;
X and Y independently represent PLA, PGA PLGA or PCL;
n, p, and k respectively represent the degree of polymerization of X, PEG, and Y, n and k independently being integers from 1 to 150, and p being an integer from 1 to 100;
j represents 0 or 1.

Most preferably, the bio-resorbable block copolymer cross-linker as defined above is of a formula selected from the group consisting of:
$(CH_2\!=\!CR_7)CO\text{-}PLA_n\text{-}PEG_p\text{-}PLA_k\text{-}CO\!-\!(CR_8\!=\!CH_2)$,
$(CH_2\!=\!CR_7)CO\text{-}PGA_n\text{-}PEG_p\text{-}PGA_k\text{-}CO\!-\!(CR_8\!=\!CH_2)$,
$(CH_2\!=\!CR_7)CO\text{-}PLGA_n\text{-}PEG_p\text{-}PLGA_k\text{-}CO\!-\!(CR_8\!=\!CH_2)$,
$(CH_2\!=\!CR_{11})CO\text{-}PCL_n\text{-}PEG_p\text{-}PCL_k\text{-}CO\!-\!(CR_{12}\!=\!CH_2)$,
$(CH_2\!=\!CR_7)CO\text{-}PEG_p\text{-}PLA_k\text{-}CO\!-\!(CR_8\!=\!CH_2)$,
$(CH_2\!=\!CR_7)CO\text{-}PEG_p\text{-}PGA_k\text{-}CO\!-\!(CR_8\!=\!CH_2)$,
$(CH_2\!=\!CR_7)CO\text{-}PEG_p\text{-}PLGA_k\text{-}CO\!-\!(CR_8\!=\!CH_2)$; and
$(CH_2\!=\!CR_{11})CO\text{-}PEG_p\text{-}PCL_k\text{-}CO\!-\!(CR_{12}\!=\!CH_2)$;
wherein $R_7$, $R_8$, n, p and k are as defined above.

Polymer

As will be clear to one of skill in the art the polymer of the invention is a bio-resorbable (i.e. hydrolyzable) cross-linked polymer. In particular the polymer of the invention is constituted of at least one chain of polymerized monomers as defined above, which at least one chain is cross-linked by bio-resorbable block copolymer cross-linkers as defined above.

Advantageously, the polymer of the invention is swellable, i.e. has the capacity to absorb liquids, in particular water. Therefore this type of polymer is called hydrogel.

As will also be clear to one of skill in the art, and by way of example, the monomers of the invention may also be represented as follows:

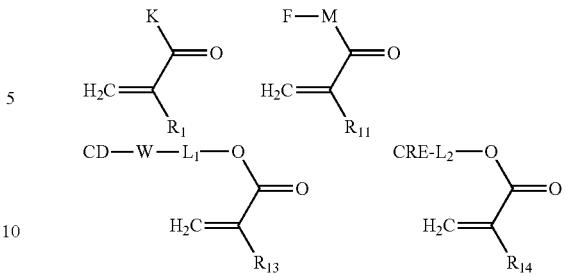

Upon polymerization the monomers of the invention may then be represented as follows:

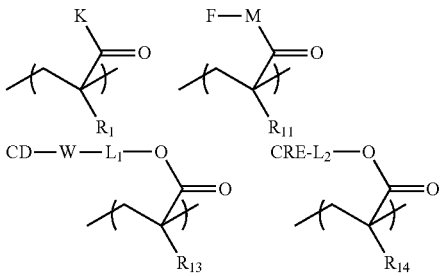

Preferably, the monomer of formula (I) as defined above is selected from the group consisting of sec-butyl acrylate, n-butyl acrylate, t-butyl acrylate, t-butyl methacrylate, methylmethacrylate, N-dimethyl-aminoethyl(methyl)acrylate, N,N-dimethylaminopropyl-(meth)acrylate, t-butylaminoethyl(methyl)acrylate, N,N-diethylaminoacrylate, acrylate terminated poly(ethylene oxide), methacrylate terminated poly(ethylene oxide), methoxy poly(ethylene oxide) methacrylate, butoxy poly(ethylene oxide) methacrylate, acrylate terminated poly(ethylene glycol), methacrylate terminated poly(ethylene glycol), methoxy poly(ethylene glycol) methacrylate, butoxy poly(ethylene glycol) methacrylate.

Most preferably, the monomer of formula (I) as defined above is poly(ethylene glycol) methyl ether methacrylate.

Besides, it is preferred that F is selected from the group constituted of COOH, COO$^-$, SO$_3$H, SO$_3^-$, PO$_4$H$_2$, PO$_4$H$^-$, PO$_4^{2-}$, NR$_9$R$_{10}$, NR$_9$R$_{12}$R$_{10}^+$, R$_9$, R$_{10}$ and R$_{12}$ independently representing H or a $C_1$-$C_6$ alkyl, a $C_1$-$C_{20}$ alkyl group, a $C_5$-$C_{20}$aryl group, a (5-30-members)heteroaryl group containing an heteroatom chosen in the group consisting of O, N or S, a O—$C_5$-$C_{20}$aryl group and a O-(5-30-members) heteroaryl group, a crown ether, and a cyclodextrin.

Preferably, the charged, ionisable, hydrophilic, or hydrophobic monomer is a cationic monomer, advantageously selected from the group consisting of (methacryloyloxy) ethyl phosphorylcholine, 2-(dimethylamino)ethyl(meth) acrylate, 2-(diethylamino)ethyl(meth)acrylate and 2-((meth) acryloyloxy)ethyl]trimethylammonium chloride. More advantageously the cationic monomer is diethylamino)ethyl (meth)acrylate. Advantageously the polymer according to the present invention is obtainable by using between 1 and 30 mol % of the above-mentioned cationic monomer based on the total amount of the monomer, more advantageously between 10 and 15 mol %.

In another advantageous embodiment, the charged, ionisable, hydrophilic, or hydrophobic monomer is an anionic monomer advantageously selected from the group consisting of acrylic acid, methacrylic acid, 2-carboxyethyl acrylate, 2-carboxyethyl acrylate oligomers, 3-sulfopropyl (meth)acrylate potassium salt and 2-(methacryloyloxy)ethyl]dimethyl-(3-sulfopropyl)ammonium hydroxide. Advantageously the polymer according to the present invention is obtainable by using between 1 and 30 mol % of the above-mentioned anionic monomer based on the total amount of the monomer, more advantageously between 10 and 15 mol %.

In an advantageous embodiment, F is a cyclodextrin and the charged, ionisable, hydrophilic, or hydrophobic monomer has the following formula (VI):

$$(CH_2=CR_{13})COO-L_1-W-CD \qquad (VI)$$

wherein:
$R_{13}$ represents H or a $C_1$-$C_6$ alkyl;
$L_1$ represents a linker moiety having from 1 to 20 carbon atoms optionally substituted by a hydroxyl group;
W represents a —NH—, —CO—, —NH—$R_{19}$—, —CO—R19-CO—, or -triazolyl-$R_{20}$-group in which $R_{19}$ and $R_{20}$ represent independently of each other a $C_1$-$C_6$ alkyl group;
—CD represents a cyclodextrin.

Advantageously the polymer according to the present invention is obtainable by using between 1 and 40 mol %, typically between 1 and 20 mol % of the above-mentioned monomer of formula (VI) based on the total amount of the monomer.

In the present invention, the cyclodextrin can be any known cyclodextrin, in particular selected in the group consisted of beta-cyclodextrin, methyl-beta-cyclodextrin, gamma-cyclodextrin or hydroxypropyl-gamma-cyclodextrin. Advantageously, it is beta-cyclodextrin.

Examples of (meth)acrylic structures bearing cyclodextrin residue are proposed in the following references: Macromol Chem Phys 2009, 210, 2107; Macromol Chem Phys 2010, 211, 245; J polym Sci 2009, 47, 4267.

In another advantageous embodiment, F is a crown ether and the charged, ionisable, hydrophilic, or hydrophobic monomer has the following formula (VII):

$$(CH_2=CR_{14})COO-L_2-CRE \qquad (VII)$$

wherein:
$R_{14}$ represents H or a $C_1$-$C_6$ alkyl;
$L_2$ represents a linker moiety having from 1 to 20 carbon atoms optionally substituted by a hydroxyl group, advantageously chosen in the group consisting of $C_1$-$C_6$ alkyl and $C_1$-$C_6$ alkyl ($OC_1$-$C_6$ alkyl) the alkyl group being optionally substituted by an hydroxyl group;
CRE represents a crown ether.

Advantageously the polymer according to the present invention is obtainable by using between 1 and 50 mol %, typically between 1 and 20 mol % of the above-mentioned monomer of formula (VII) based on the total amount of the monomer.

Examples of (meth)acrylic structures bearing crown ether residue are proposed in the following references: Polymer 2004, 45, 1467; Macromolecules 2003, 36, 1514.

In still another advantageous embodiment, F is selected from the group constituted of a $C_5$-$C_{20}$ aryl group, a (5-30-members) heteroaryl group containing an heteroatom chosen in the group consisting of O, N or S, a O—$C_5$-$C_{20}$aryl group and a O-(5-30-members) heteroaryl group and the charged, ionisable, hydrophilic, or hydrophobic monomer has the following formula (VIII):

$$(CH_2=CR_{22})COO-L_4-Ar \qquad (VIII)$$

wherein:
$R_{22}$ represents H or a $C_1$-$C_6$ alkyl;
$L_4$ represents a linker moiety having from 1 to 20 carbon atoms optionally substituted by a hydroxyl group, advantageously chosen in the group consisting of $C_1$-$C_6$ alkyl and $C^1$—$C_6$ alkyl ($OC_1$-$C_6$ alkyl), the alkyl group being optionally substituted by an hydroxyl group;
Ar represents a $C_5$-$C_{20}$ aryl, (5-30-members) heteroaryl containing an heteroatom chosen in the group consisting of O, N or S, O—$C_5$-$C_{20}$aryl or O-(5-30-members) heteroaryl group containing an heteroatom chosen in the group consisting of O, N or S.

Advantageously the polymer according to the present invention is obtained by using between 1 and 50 mol %, typically between 1 and 30 mol % of the above-mentioned monomer of formula (VIII) based on the total amount of the monomer, more advantageously between 5 and 15 mol %.

Advantageously the charged, ionisable, hydrophilic, or hydrophobic monomer of formula (VIII) as defined above is selected from the group consisting of 2-(4-benzoyl-3-hydroxyphenoxy)ethyl(meth)acrylate, 2-hydroxy-3-phenoxypropyl(meth)acrylate, ethylene glycol phenyl ether (meth)acrylate, benzyl methacrylate, 9H-carbazole-9-ethylmethacrylate.

It is also preferred that $L_1$, $L_2$ and M are of the following formula:

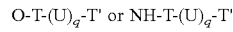
$$O\text{-}T\text{-}(U)_q\text{-}T' \text{ or } NH\text{-}T\text{-}(U)_q\text{-}T'$$

wherein T and T', identical or different, represent a $C_1$-$C_6$ alkyl chain optionally substituted by one or more hydroxyl, oxo, or amino group, U represents an hydrolysable function, such as an ester, amide, a disulfide, an amino-oxy or anhydride function, and q represents an integer from 0 to 2 for M and from 1 to 2 for $L_1$ and $L_2$.

The polymer of the invention can be readily synthesized by numerous methods well-known to one of skill in the art if the macromolecules are loaded after its preparation. By way of example, the polymers of the invention can be obtained by suspension polymerization using either a direct or an inverse process as described below and in the Examples.

A direct suspension may proceed as follows: (a) stirring or agitating a mixture comprising (i) at least one monomer as defined above, and at least one bio-resorbable block copolymer cross-linker; (ii) a polymerization initiator present in amounts ranging from 0.1 to approximately 2 parts per weight per 100 parts by weight of the monomers; (iii) a surfactant in an amount no greater than about 5 parts by weight per 100 parts by weight of the monomers, preferably no greater than about 3 parts by weight and most preferably in the range of 0.5 to 1.5 parts by weight; and (iv) water to form an oil in water suspension; and (b) polymerizing the monomer(s) and the bio-resorbable block copolymer cross-linker.

An inverse suspension may proceed as follows: (a) stirring or agitating a mixture comprising: (i) at least one monomer as defined above, and at least one bio-resorbable block copolymer cross-linker; (ii) a polymerization initiator present in amounts ranging from 0.1 to approximately 2 parts per weight per 100 parts by weight of the monomers; (iii) a surfactant in an amount no greater than about 5 parts by weight per 100 parts by weight of the monomers, preferably no greater than about 3 parts by weight and most preferably in the range of 0.5 to 1.5 parts by weight; and (iv)

oil to form a water in oil suspension; and (b) polymerizing the monomers and the bio-resorbable block copolymer cross-linker.

Therefore in this case the process of preparation of the macromolecule loaded polymer according to the present invention comprises the impregnation of the preformed polymer with the macromolecule. For instance, the polymer in a dry form is made to swell in a solution containing a predetermined amount of the macromolecule for 1 h to 24 h depending on the macromolecule.

The mesh size of the polymer described above should be sufficient to allow a penetration of the macromolecule inside the polymeric network. Otherwise due to the large size of the macromolecule, it will just be adsorbed on the surface and an initial burst or rapid release of macromolecule will be observed. Such mesh size can be obtained by choosing with particular attention the amount of crosslinker used.

For ionic macromolecules, the adsorption may be favour by the presence of opposite charges on the structure of hydrogel according to the present invention, in particular due to use of monomer of formula (V) to achieve high complexation efficiencies.

The process for the preparation of the macromolecule loaded polymer according to the present invention can also be different. It comprises the step of mixing of the macromolecules with a solution containing the monomers and the crosslinker as described in above prior to the crosslinking reaction. This type of process is more advantageous since it allows higher incorporation efficiencies, a better control of the release and avoids burst effect.

The process should be designed to avoid any contact with organic solvent, and heating. In this way, the formulation of the polymer to be loaded is done with water soluble monomer and crosslinker which could polymerize at room temperature or up to 40° C.

A second important aspect is the control release of the macromolecule. The release will occur during the resorption of the polymer network so it should be controlled through various parameters like degree of crosslinking, nature of hydrolysable crosslinker and presence of specific comonomers as described in patent No. PCT/EP 2010/063227. Moreover, the polymer network should allow diffusion of the degradation products in order to maintain a suitable pH inside the polymer for the macromolecule.

Advantageously, when the crosslinking reaction is carried out by inverse suspension polymerization, the solution is a water solution.

Indeed crosslinking of the polymer chains can be achieved by several methods:

Inverse suspension polymerization: in this process, the polymerization occurs in water droplets suspended in an oil phase. The macromolecule could be mixed with hydrophilic monomers and the resorbable crosslinker in water prior to the polymerization. The reaction can be initiated by a water soluble initiator such as ammonium or potassium persulfate in presence of TEMED as catalyst at ambient temperature (Cha, Adv. Funct. Mater., 3056-3062, 2009). To avoid the use of such compounds, polymerization can also be done under gamma irradiation (photopolymerization) (Van Tomme, international Journal of Pharmaceutics, 355, 1-18, 2008).

Instead of working in a reactor to perform inverse suspension polymerization, microspheres can be formed by a drop by drop process. In this case, an aqueous solution composed by the macromolecule, hydrophilic monomers and the resorbable crosslinker in water descends through a nozzle onto an oil medium and then polymerize through thermal polymerization or photopolymerization during their descent. (Tokuyama, Reactive & Functional Polymers, 70, 967-971, 2010).

Crosslinking of (meth)acrylate groups via Michael-type addition reaction may also be envisaged. This reaction may be performed in physiological conditions.

A relatively novel process using a membrane emulsification technique developed by SPG Technology Co allows forming uniform-sized microspheres. This method may be adapted for the incorporation of bioactive compounds thanks to the double emulsion W/O/W. However, today size of the microspheres is limited to 100 µm Another method consists to firstly incorporate the bioactive compound into a nanocapsule in order to protect the drug. Then, the loaded nanocapsules are themselves loaded onto the resorbable implant preferentially in the shape of microspheres.

The nanocapsules have an average size lower than 1 µm when measured by light scattering. The incorporation of the drugs in the nanocapsules is realized during the preparation of the nanoparticules which are themselves prepared by the double emulsion method (Pharm Res 15(2): 270-5 1998, J Control Release 75(1-2): 211-24, 2001, Crit. Rev Ther Drug Carrier Syst. 2002; 19(2):99-134).

The polymer from which the nanoparticles are made is preferably chosen among polylactic acid (polylactide), polyglycolic acid (polyglycolide), lactide-glycolide copolymers, lactide-glycolide-polyethyleneglycol copolymers, polyorthoesters, polyanhydrides, biodegradable block-copolymers, poly(esters), poly(butyrolactone), poly(valerolactone), poly(malic acid) and generally polylactones and the copolymers of each of one or more of these polymers.

Macromolecule

As intended here the macromolecule as defined above can be of any type in the group selected from proteins and nucleic acids and intended for the prevention or treatment of any disease or impairment.

As indicated above, in particular where the polymer of the invention is obtained from the polymerization of at least one charged, ionisable, hydrophilic, or hydrophobic monomer, the macromolecule is loaded onto the polymer that is adsorbed on the polymer by non-covalent interactions. No particular requirement is then imposed on the macromolecules to be loaded.

In particular, the macromolecule is chosen in the group consisting of enzymes, antibodies, cytokines, growth factor, coagulation factors, hormones, in particular growth hormones, plasmids, antisense oligonucleotides, siRNA, ribozymes, DNAzymes, aptamers, advantageously from the group consisting of anti-inflammatory proteins such as infliximab and rilonacept, bone morphogentic proteins, angiogenic factors such as fibroblast growth factors, vascular endothelial growth factors and TGF-beta, inhibitors of angiogenesis such as bevacizumab or pegaptanib. Among the preferred peptides and proteins are erythropoetins, such as epoetin alpha, epoetin beta, darbepoetin, hemoglobin raffimer, and analogues or derivatives thereof; interferons, such as interferon alpha, interferon alpha-2b, PEG-interferon alpha-2b, interferon alpha-2a, interferon beta, interferon beta-1a and interferon gamma; insulins; antibodies, such as rituximab, infliximab, trastuzumab, adalimumab, omalizumab, tositumomab, efalizumab, and cetuximab; blood factors such as alteplase, tenecteplase, factor VII(a), factor VIII; colony stimulating factors such as filgrastim, pegfilgrastim; growth hormones such as human growth factor or somatropin; interleukins such as interleukin-2 and interleukin-12; growth factors such as beclapermin, trafermin, ancetism, keratinocyte growth factor; LHRH analogues such as leuprolide, goserelin, triptorelin, buserelin, nafarelin; vaccines, etanercept, imiglucerase, drotrecogin alpha.

Advantageously, the antibodies are chosen in the following group: anti-CD3 such as muromonab (in particular Othroclone OKT3® from J & J-Ortho Biotech), anti-GPIIb/IIIa such as abciximab (in particular Reopro® from Centocor-Lilly), anti-CD20 such as rituximab (in particular Rituxan® from Idec-Genentech) or Ibritumomab (in particular Zevalin® from Biogen Idec) or Tositumomab-1131 (in particular Bexxar® from Corixam-GSK), anti-CD25 such as daclizimab (in particular Zenapax® from Roche) or basilixamab (in particular Simulect® from Novartis), anti-RSV such as Palivizumab (in particular Synagis® from MedImmune), anti-TNFa such as Infliximab (in particular Remicade® from Centocor) or Adalimumab (in particular Humira® from Abbott), anti-HER2 such as Trastuzumab (in particular Herceptin® from Genectech), immunotoxin such as Gemtuzumab (in particular Mylotarg® from Wyeth), anti-CD52 such as Alemtuzumab (in particular Campath®R-1H from Millennium-ILEX), anti-IgE such as Omalizumab (in particular Xolair® from Genentech), anti-CD11a such as Efalizumab (in particular Raptiva® from Genentech), anti-EGFR such as Cetuximab (in particular Erbitux® from Imclone Systems), anti-VEGF such as Bevacizumab (in particular Avastin® from Genentech) and anti-4a-integrin such as Natalizumab (in particular Tysabri® from Biogen Idec).

Advantageously, the hormones are chosen in the following group: somatropin such as Norditropin® from Novo Nordisk Inc, lutropin alfa such as Luveris® from Serono, Inc., follitropin alfa such as Gonal-F® from Serono, Inc, Sermorelin acetate such as Geref® from Serono, Inc., Epoetin alfa such as Epogen® from Amgen, Inc., and pegvisomant such as Somavert® from, Sensus Corporation.

Advantageously, the cytokines are chosen in the following group: Interferon gamma-1b such as Actimmune® from InterMune, Inc., Interferon beta-1a such as Avonex® from Biogen idec, interferon alfa-2a such as Roferon-A® from Hoffmann-La Roche, Inc, interferon beta-1b such as Betaseron® from Chiron Corp. & Berlex Laboratories, interferon alfa-2b such as Intron®A from Schering Corporation, Interferon alfa-n1 such as Wellferon® from Glaxo Wellcome Inc., peginterferon alfa-2a such as Pegasys® from Hoffman-La Roche Inc. and Human recombinant GM-CSF such as Leucomax® from Novartis.

Advantageously, the cytokines are chosen in the following group of bone morphogenetic proteins (BMP): BMP-2, -3, -3b, -4, -5, -6, -7, -8, -9, -11, -12, -13, -14, with a preference for BMP-2, -4, -6, -7 and -9 as bone and cartilage inducers for tissue-engineering purpose (Bessa, 1-13, 2008, *Journal of Tissue Engineering and Regenerative Medicine*, Bessa, 81-96, 2008, *Journal of Tissue Engineering and Regenerative Medicine*).

Advantageously, pro-angiogenic factors are chosen in the group consisting of Angiopoietins, Angiogenins, Ephrins, E-selectin, Fibroblast growth factors (FGF) (Acidic FGF, Basic FGF, FGF3-9), Hepatocyte growth factor, Insulin-like growth factor, Platelet derived growth factor (PDGF), Thrombospondin, Transforming growth factor-β (TGF-β), Tumor necrosis factor-α (TNF-α), Vascular endothelial growth factors (VEGF) (VEGFA-121, -145, -165, -189, -206, VEGFB, VEGFC, VEGFD, VEGFE, Placental growth factor) (Lei, 121-132, 2004, *Basic Research in Cardiology*).

Nucleic acids are macromolecules with medical applications. These therapeutics include plasmids containing transgenes, oligonucleotides, aptamers, ribozymes, DNAzymes, and small interfering RNAs. These drugs can be used to mitigate disease either prophylactically or at a very early stage, preventing disease progression and its complications. Among the therapeutic nucleic acids can be distinguished schematically plasmids, which are double-stranded circular DNA of high molecular weight (>1000 base pair). Currently, only one plasmid (Gendicine) is marketed in China since 2004, encoding for the tumor suppressor p53 protein. This plasmid was transferred into human cells using adenovirus carrier. Antisense oligonucleotides are single-stranded DNA with a length of 12-28 nucleotides. Only one antisense oligonucleotide is marketed under the name Vitravene (fomivirsen sodium) with indication for the treatment of cytomegalovirus retinitis induced in patients with AIDS. The RNA interference (SiRNAs) are segments of double-stranded RNA of 21 to 23 nucleotides complementary to a region of a messenger RNA to be degraded in the cytoplasm of the cell. Currently there are no so-RNA on the market in spite of encouraging clinical trials for the product bevasiranib (Opko Health, Inc., Miami, Fla., USA; phase III) and ALN-RSV01 (Alnylam, Cambridge, Mass., USA, Phase II).

Aptamers are single or double stranded RNA or DNA that interact specifically with a protein to inactivate it. An aptamer is marketed (Macugen, pegaptanib, Eyetech/Pfizer), which acts as inhibitor of VEGF in treatment of Age-related macular. Aptamers are fragile molecules, for example an unmodified aptamer directed against thrombin has an in vivo half-life of 108 seconds (Ng et al., 2006). Chemical modifications increase their stability towards nucleases. Resistant aptamers are obtained by modification of 2' ribose's hydroxyl group with fluorine, amino group, methyl or by adding a polyethylene glycol molecule. The Macugen aptamer modified with these substitutions has a half-life of 18 hours in human plasma (Ng, 123-132, 2006, *Nature Reviews*). Compared to antibodies, aptamers synthesis is simpler and therefore more economical unlike antibodies that require a complex infrastructure-based on protein expression systems. Aptamers can be considered as "chemical antibodies," which combine the advantages of antibodies (specificity of antigen recognition) with an economic manufacturing.

All these different type of nucleic acids could be loaded in the polymer according to the present invention.

In a particular embodiment, the resorbable polymer is combined non covalently during its synthesis with cationic polymers for nucleic acid loading such as poly(allylamine hydrochloride), polydiallyldimethylammonium, polyethylenimine, poly(L-lysine), polydopamine, chitosan and polyamidoamine dendrimers. Before its use, the polymer is loaded with nucleic acids which are absorbed by an ionic mechanism.

Resorbable implant comprises a marker such as a dye for controlling its delivery from the syringe towards the hub of the catheter or needle, or an imaging agent for its visibility in the body during or after injection (barium sulphate, tungsten or titanium powder, iodinated compounds, paramagnetic compounds such as dextran-magnetite particles, Gadolinium derivatives, a radionucleide).

Form of the Polymer

Preferably, the polymer of the invention is in the form of a film, a foam, a particle, a lump, a thread, or a sponge, and most preferably is in the form of a spherical particle. The spherical particle is preferably a microsphere, i.e. has a diameter upon swelling (i.e. upon hydration), ranging from 1 to 5000 µm, more preferably ranging from 50 to 2500 µm, typically from 50 and 1000 µm (to be not phagocytised and pass easily through small needles), more advantageously ranging from 100 to 300 µm or from 300 to 500 µm or from 500 to 700 µm, or from 700 to 900 µm, or from 900 to 1200 µm. The spherical particles should have a diameter small enough to be injected by needles or catheter, in particular small needles diameter but big enough to avoid engulfment by macrophage. The spherical particles can be injected after swelling and therefore their diameter in this case could be of between 100 to 300 µm. Their swelling could also be limited, for example to about 50% of their total capacity of fluid absorbtion, before injection in order for them to swell mainly after implantation by absorbing physiological fluids such as the fluid from wounds, from interstitial milieu and from blood fluids.

In order to swell, the polymer of the invention may absorb, preferably in a controlled way, liquids, such as water, in particular from solutions commonly used, such as physiological saline, buffered solution, glucose solution, plasma, ionic or non ionic iodinated contrast media, iron oxide based contrast media for magnetic resonance imaging, drug solutions, or any sterile apyrogen liquid that is injectable in the human or animal body. A defined and limited quantity of water is absorbed by the polymer of the invention, thereby enabling, where the polymer is a spherical particle, to anticipate the diameter upon swelling.

Pharmaceutical and Therapeutical Use of the Polymer

Advantageously also, resorption of the polymer of the invention depends on hydrolysis and not on an enzymatic mechanism. Resorption speed may thus be readily controlled by modulating the type and amount of bio-resorbable cross-linker and monomer as defined above.

Equally advantageous, resorption of the polymer of the invention may range from a few hours to a few weeks or even a few months depending on the type and amount of bio-resorbable cross-linker and monomer as defined above. In addition, the polymer of the invention develops only a limited local inflammatory response upon implantation, since the degradation products of the polymer are non toxic and quickly eliminated.

The pharmaceutical composition thus defined contains a pharmaceutically acceptable carrier, advantageously intended for administration by injection.

Exemplary of pharmaceutically acceptable carrier includes but are not limited to water for injection, saline, starch, hydrogel, polyvinylpyrrolidone, polysaccharide, hyaluronic acid ester, and plasma. The pharmaceutical composition can also contain a contrast agent for Xray, MR or US imaging, a buffering agent, a preservative, a gelling agent, a surfactant. Advantageously, the pharmaceutically acceptable carrier is saline or water for injection.

The pharmaceutical composition should have a viscosity acceptable for injection. In particular it could be of between 10 and 100 cP, more advantageously of between 20 and 30 cP when measured at 25° C. with Couette viscosimeter.

In particular, the injectable pharmaceutical composition comprises (a) a polymer according to the present invention loaded or not with the macromolecule having a spherical shape of a diameter of between 50 and 500 µm upon total or limited swelling and a resorption time of between two days to 3 weeks;

(b) a polymer according to the present invention loaded or not with the macromolecule having a spherical shape of a diameter of between 50 and 500 µm upon total or limited swelling and a resorption time of between one to 3 months; and (c) at least one pharmaceutically acceptable excipients;

wherein at least one of the polymer (a) or (b) is loaded with a macromolecule, advantageously polymer (a) is loaded with the macromolecule.

Both of the polymers (a) and (b) could be loaded with a macromolecule, the macromolecule being identical or different.

In particular, the pharmaceutically excipients can be a hydrogel, for example having a resorption time of at most 1 week.

Advantageously the particles of polymer (a) and of polymer (b) have the same density.

In a particular advantageous embodiment, the spherical particles of polymer (a) and (b) have all the same diameter upon total or limited swelling, in particular chosen in the range of 100 to 300 µm or in the range of 300 to 500 µm, more advantageously in the range of 100 to 300 µm.

The proportion of polymer (a) and (b) in the pharmaceutical composition can be of between 20 to 80% by weight, advantageously of between 40 and 70% by weight, still more advantageously of 60% by weight.

In another advantageous embodiment, the proportion of polymer (a) is identical to the proportion of polymer (b) in the pharmaceutical composition.

In another advantageous embodiment, their proportions are differents. For example in this case, their respective ratio is: polymer (a) between 60 and 80%, advantageously 70% by weight, and polymer (b) between 20 and 40%, advantageously 30% by weight of the total amount of polymer (a)+(b).

In a particular embodiment, the spherical particles of polymer (a) and (b) do not have the same diameter. Advantageously the diameter of the spherical particles of polymer (a) is of between 100 and 300 µm and the diameter of the spherical particles of polymer (b) is of between 300 and 500 µm.

In another advantageous embodiment, the spherical particles of polymer (a) do not have all the same diameter. Some of them have a diameter of between 100 and 300 µm and the other a diameter of between 300 and 500 µm, advantageously half of them have a diameter of between 100 and 300 µm and the other half a diameter of between 300 and 500 µm.

In a particular composition according to the present invention the spherical particles of polymer (a) and the spherical particles of polymer (b) have all a diameter of between 100 and 300 µm, the proportion of particles of polymer (a) being 70% by weight whereas the proportion of particles of polymer (b) is 30% by weight.

In another particular composition according to the present invention the spherical particles of polymer (a) and the spherical particles of polymer (b) have all a diameter of between 300 and 500 µm, the proportion of particles of polymer (a) being 70% by weight whereas the proportion of particles of polymer (b) is 30% by weight.

In a further particular composition according to the present invention the spherical particles of polymer (a) have all a diameter of between 100 and 300 µm, and the spherical particles of polymer (b) have all a diameter of between 300 and 500 µm, the proportion of particles of polymer (a) being 50% by weight whereas the proportion of particles of polymer (b) is 50% by weight.

In still a further particular composition according to the present invention, half of the spherical particles of polymer (a) have all a diameter of between 100 and 300 µm, the other half have all a diameter of between 300 and 500 µm and the spherical particles of polymer (b) have all a diameter of between 300 and 500 µm, the proportion of particles of polymer (a) being 50% by weight whereas the proportion of particles of polymer (b) is 50% by weight.

After injection this pharmaceutical composition forms a depot in the site of injection.

These compositions are particularly useful for filling of and/or camouflaging and/or correcting wrinkles, fine lines, skin cracks, cutaneous depressions, lipodystrophies, facial hemiatrophy, and/or scars, in particular acne scars and/or smoothing out irregularity of the skin and/or as a matrix for cellular culture and/or for tissue engineering. In fact, a large part of the particles of polymer (a) is resorbed quickly in situ to promote tissue ingrowth in the depot. In particular in order to increase tissue ingrowth, the loaded macromolecule is chosen in the group consisting of growth factors (VEGF, bFGF, TGF-β, PDGF, insulin, angiopoietin).

The resorption is progressive and develops in three phases to help the body to consider the depot as a matrix and not as a foreign body.

After injection there are several phases: During the acute phase (a few days) the composition has a bulking effect. There is water intake (controlled) of the composition due to the swelling of the particles of polymer (a) and at a lesser degree of polymer (b). There is also proteins adsorbtion and cells adhesion on the implanted composition according to the present invention. During the Second phase (which last weeks or months) occurs the resorption of the particles of polymer (a), which creates a porosity of the bulk facilitating its penetration by cells (fibroblasts for example), beginning of collagen deposit and fibrosis (first network structure). The particles of polymer (a) are replaced by collagen or hyaluronic acid phase. These particles are designed to be very supple and behave as a viscous gel facilitating the injection and the stability of the particles of polymer (b). The proportion of these particles will be maintained relatively low in order to avoid a global inflammatory response directed towards the depot. In a third phase, during the next months, there is a resorption of the particles of polymer (b) which will open new channels for a total replacement by tissular growth and its vascularisation (fibrovascular ingrowth).

Due to this type of composition the porosity of the depot obtained after injection increases over time further to the resorption of the polymer according to the present invention. The rate and the importance of the resorption are controlled by the polymer used for preparation of the composition and therefore by their time of resorption. The time of resorption is dependent on the type of monomer used for the preparation of the polymer and in particular on the type and amount of the crosslinker.

Therefore, the polymer according to the present invention allow the obtention of injectable suspension of a combination of resorbable microspheres having various sizes and resorption times to produce in a controlled way in situ after implantation a tissue scaffold or matrix, which is transformed by resorption in a porous structure designed to be colonized by a tissue ingrowth, the tissue ingrowth being increased by the controlled release of the macromolecule loaded in the polymer. In order to increase tissue ingrowth, the polymer according to the present invention can be loaded with macromolecules as described above. This release may be controlled in terms of delivery rate according to the resorption rate of the polymer containing them. A combination of several polymers containing different macromolecules can be used to obtain a sequence of macromolecules delivery. For example a composition for wound dressing would insure a delivery of VEGF during the first week and a delivery of TGF-β, PDGF or BFGF during the following weeks.

The properties of the porous structure (pore size and connection, time of appearance) are designed by controlling several factors: nature of resorbable microspheres, proportions of the different resorbable microspheres associated in the suspension, sizes of the different resorbable microspheres.

The present invention also concern an implant, in particular for implantation into skin, or other tissues and organs, in particular deep organs such as kidney or liver, brain, spinal cord, bones defects, internal anatomical spaces, such as peritoneum and meningeal spaces, body cavities, ducts and vessels. The implant is implanted where the treatment with the macromolecule which is loaded in the polymer is necessary.

The local therapy by using this type of implant concern organs which differ in their location, from the surface of the body as skin, less accessible like bones, or deep organs such kidney or liver. The accessibility to organs are different, very accessible for skin when a wound dressing assisted with a macromolecule such as bFGF, VEGF or EGF, is required, more invasive for delivery of proteins in order to assist bone healing, and requiring sophistically chirurgical procedures to supply locally cytotoxic or anti-angiogenic agents in the environment of tumor in an internal organ (liver, lung). Accordingly, properties of the polymer (shape, composition, degradability, release performances) will be different and adapted to a specific treatment.

Depending on the type of the intended therapeutical or cosmetic application, the site of application is different. If the intended application concerns the face, the implant is injected in the soft tissue, in particular subcutaneously or intradermally.

If the implant is injected in the tissue, it can increase the tissue volume.

In a particular embodiment, the pharmaceutical composition comprises the polymer of the invention in a dry form, such as a lyophilized form.

The pharmaceutical composition of the invention will be preferably used in the frame of embolization, in particular for uterine artery embolization (UAE), or for haemostasis. It can also be used in the treatment of benign or malignant tumors, arteriovenous malformations, gastrointestinal bleeding, epistaxis, primary post-partum haemorrhage and/or surgical haemorrhage.

The pharmaceutical composition of the invention is also preferably used for treating cancer. In this case, treatment may occur by delivery of anti-cancer macromolecules loaded on the polymer of the invention and possibly by embolization, in particular by repeated embolization. In particular the cancer of interest is chosen in the group consisting of liver lesions, typically hepatocellular carcinoma (HCC), kidney lesions and/or uterine fibroids.

The present invention also concerns the use of the implant as described above, of the polymer according to the present invention or of the composition as described above for filling of and/or camouflaging and/or correcting wrinkles, fine lines, skin cracks, cutaneous depressions, lipodystrophies, facial hemiatrophy, and/or scars, in particular acne scars and/or smoothing out irregularity of the skin and/or as a matrix for cellular culture and/or for tissue engineering.

In a particular aspect of the invention, it is possible to use the polymer and/or the composition and/or the implant according to the invention as a matrix for cellular culture, with applications in particular in cosmetic surgery, dermatology, rheumatology and gastroenterology. Actually, the resorbable polymer according to the invention, in particular in the form of the composition as described above, is a good three-dimensional substrate for supporting the growth of various types of cells.

In cosmetic surgery, it is possible to cite applications for implants for filling in wrinkles or hollows.

In dermatology, it can be used for healing chronic wounds: as a matrix, it makes possible the tangential development of the process of healing and the prevention of budding in the case of hypertrophic healing.

In rheumatology and orthopedics, the use of the polymer and/or the composition and/or the implant according to the invention as a matrix for the cellular culture is particularly suitable for the repair of the cartilage by chondroinduction.

Relative to the applications of the polymer and/or the composition and/or the implant as a three-dimensional substrate for the cellular growth of autologous cells to prepare tissue engineered implantable scaffolds for bone, cartilage, skin, and other organs reconstruction.

The polymer and/or the composition and/or the implant according to the present invention can also be used for variety of soft tissue repair and augmentation procedure, in particular on the facial tissue such as for example camouflaging scars, filling depressions, smoothing out irregularity, correcting asymmetry in facial hemiatrophy, facial lipodystrophy and camouflaging age-related wrinkles. It can be used in reconstructive surgery to restore form and/or function to soft tissues altered by age, trauma, disease, or other defect. It can also replace facial fat loss (lipoatrophy), for example, to provide volume in areas of the patient's soft tissues which suffer from fat, collagen or muscle loss for reasons of old age or disease.

Definition

As used herein, the term "alkyl" refers to a straight or branched saturated monovalent hydrocarbon radical, having the number of carbon atoms as indicated. For example, the term "$C_{1-6}$-alkyl" includes $C_1$, $C_2$, $C_3$, $C_4$, $C_5$, and $C_6$ alkyl groups. By way of non-limiting example, suitable alkyl groups include methyl, ethyl, propyl, iso-propyl, butyl, iso-butyl, tert-butyl, pentyl and hexyl. In one aspect of the present invention ranges of alkyl groups are: $C_{1-6}$-alkyl, $C_{1-5}$-alkyl, $C_{1-3}$-alkyl and $C_{1-2}$-alkyl.

As used herein, the term "aryl" refers to monovalent unsaturated aromatic carbocyclic radical having one, two, or three rings, which may be fused or bicyclic. In one aspect of the present invention, the term "aryl" refers to an aromatic monocyclic ring containing 5 or 6 carbon atoms, an aromatic bicyclic or fused ring system containing 7, 8, 9 or 10 carbon atoms, or an aromatic tricyclic ring system containing up to 10 carbon atoms. By way of non-limiting example, suitable aryl groups include phenyl, biphenyl, anthracenyl, thiophenyl. In one aspect of the present invention ranges of aryl groups are: $C_{5-20}$-aryl, $C_{5-10}$-aryl, $C_{5-8}$-aryl and $C_{6-7}$-aryl.

The term "(5-30members) heteroaryl" refers to monovalent unsaturated aromatic heterocyclic radicals containing 5 to 30 members having one, two, three or more rings containing at least one hetereoatom, in particular O, N or S, advantageously two heteroatoms, in particular 3 heteroatoms, which may be fused or bicyclic. Suitably, the term "heteroaryl" encompasses heteroaryl moieties that are aromatic monocyclic ring systems containing five members of which at least one member is a N, O or S atom and which optionally contains one, two or three additional N atoms, an aromatic monocyclic ring having six members of which one, two or three members are a N atom, aromatic bicyclic or fused rings having nine members of which at least one member is a N, O or S atom and which optionally contains one, two or three additional N atoms or aromatic bicyclic rings having ten members of which one, two or three members are a N atom. By way of non-limiting example, suitable heteroaryl groups include furanyl, pyridyl, phthalimido, thiophenyl, pyrrolyl, imidazolyl, pyrazolyl, thiazolyl, isothiazolyl, oxazolyl, oxadiazolyl, pyronyl, pyrazinyl, tetrazolyl, thionaphthyl, benzofuranyl, indolyl, oxyindolyl, isoindolyl, indazolyl, indolinyl, azaindolyl, benzopyranyl, coumarinyl, isocoumarinyl, quinolyl, isoquinolyl, cinnolinyl, quinazolinyl, benzoxazinyl, chromenyl, chromanyl, isochromanyl, thiazolyl, isoxazolyl, isoxazolonyl, isothiazolyl, triazolyl, oxadiazolyl, thiadiazolyl, triazyl carbazol, porphyrin, triphenylenes and pyridazyl, advantageously pyridine, carbazol, porphyrin, triphenylenes.

EXAMPLES

Example 1

1. Synthesis of the Bio-Resorbable Cross-Linker by the HEMA/PEGMA Method

First Step:

In a dry schlenk containing a magnetic stirring bar, lactide (2.22 g; 0.0154 mol) and hydroxyethyl methacrylate (0.75 mL; 0.0062 mol) were dissolved in 5 ml of toluene under nitrogen. The reaction was initiated by introducing a toluene solution of $Sn(Oct)_2$ (8 mg) into the above system. After 20 h at 90° C., 5 ml of chloroform was added to dilute the reaction mixture and the formed polymer was purified by precipitating in a large volume of petroleum ether. Yield 94%.

$^1$H NMR in $CD_3COCD_3$: 1.53 (m, $CH_3$, PLA), 1.91 (s, $CH_3$, methacrylate), 4.38 (m, $CH_2$, HEMA), 5.17 (m, CH, PLA), 5.65-6.10 (m, $CH_2$=C).

Second Step:

The polymer formed in the first step was further modified through the hydroxyl group at the end of PLA chain by reacting with methacryloyl chloride. The preformed polymer (1.07 mmol of OH group, 1 eq.) was dissolved in anhydrous $CH_2Cl_2$ (2.5 ml) in a three necked flask equipped with magnetic stirrer and a dropping funnel. The content of the flask was cooled to 0° C. and triethylamine (1.5 eq.; 0.0016 mol) was added. The solution was stirred and then methacryloyl chloride (1.5 eq.; 0.0016 mol) in $CH_2Cl_2$ (2.5 ml) was added dropwise to the solution. The stirring was continued 1 h at 0° C. and then one night at room temperature. The triethylamine salt was removed by filtration and the polymer was precipitated in a large volume of petroleum ether. Yield: 95%.

$^1$H NMR in $CD_3COCD_3$: 1.53 (m, $CH_3$, PLA), 1.91 (m, $CH_3$, methacrylate), 4.39 (m, $CH_2$, HEMA), 5.17 (m, CH, PLA), 5.65-6.16 (m, $CH_2$=C).

2. Synthesis of the Bio-Resorbable Cross-Linker by the PEG Method

First Step:

In a dry schlenk containing a magnetic stirring bar, the PEG600 (10 g; 0.0167 mol) was reacted with d,l-lactide (7.2 g; 0.05 mol) and glycolide (5.8 g; 0.05 mol) for 20 h at 115° C. using stannous octoate as catalyst (114 mg) under argon. Then, the polymer was dissolved in chloroform, precipitated in a large volume of petroleum ether/diethyl ether (50/50) then in pure petroleum ether.

$^1$H NMR in CDCl$_3$: 1.55 (m, CH$_3$, PLA), 3.64 (m, CH$_2$, PEG), 4.25 (m, CH$_2$, PEG), 4.80 (m, CH$_2$, PGA), 5.20 (m, CH, PLA)

Second Step:

The polymer formed in the first step was further modified through the hydroxyl groups at the end of PLGA by reacting with methacrylic anhydride. In a typical reaction, the preformed polymer (4.91 g) was dissolved in degased ethyl acetate (25 ml) in a dry Schlenk tube equipped with magnetic stirrer. The content of the flask was cooled to 0° C. and methacrylic anhydride (3.3 ml.; 0.022 mol) was added dropwise to the solution under an argon flow. The stirring was continued 1 h at 0° C. and then 6 h at 80° C. After cooling, the polymer was precipitated three times in a large volume of petroleum ether.

$^1$H NMR in CDCl$_3$: 1.56 (m, CH$_3$, PLA), 1.94 (m, CH$_3$, methacrylate), 3.63 (m, CH$_2$, PEG), 4.29 (m, CH$_2$, PEG), 4.80 (m, CH$_2$, PGA), 5.20 (m, CH, PLA), 5.64-6.15 (m, CH$_2$=C)

A series of bio-resorbable crosslinkers has been synthesized by varying the molecular weight of the PEG, and the length and the chemical composition of the resorbable segment (Table 1).

TABLE 1

Resorbable crosslinkers

| Code | PEG (g · mol$^{-1}$) | Lact/glyc (mol %) | PD$_{res\ segment}$* |
|---|---|---|---|
| EG-PLGA$_{12}$ | 44 | 50/50 | 12 |
| TEG-PLGA$_{12}$ | 176 | 50/50 | 12 |
| TEG-PLGA$_{20}$ | 176 | 50/50 | 20 |
| TEG-PLA$_{12}$ | 176 | 100/0 | 12 |
| PEG$_{13}$PLGA$_{12}$ | 600 | 50/50 | 12 |
| PEG$_{13}$PLA$_{12}$ | 600 | 100/0 | 12 |
| PEG$_{22}$PLGA$_{12}$ | 1000 | 50/50 | 12 |
| PEG$_{22}$PLGA$_{8}$ | 1000 | 50/50 | 8 |
| PEG$_{13}$PLA$_{12}$ | 1000 | 100/0 | 12 |
| PEG$_{13}$PCL$_{8}$ | 600 | PCL 100 | 6 |

*: polymerization degree of resorbable segment of resorbable crosslinkers

Example 2: Synthesis of Resorbable Hydrogels

1. In Organic Solvent G#1

Resorbable crosslinker PEG$_{22}$PLGA$_{12}$ (5% mol) was dissolved in 1 ml toluene and degased under nitrogen. To this were added poly(ethylene glycol) methyl ether methacrylate Mw 300 (95% mol) and hexanethiol (3% mol/mol of PEGMA). 1% mol of AIBN were dissolved in 1 ml of toluene and added to the monomers solution. The mixture was heated at 80° C. for 8 h. After cooling, the polymer was washed twice with acetone and then distilled water.

Hydrogel discs (7 mm thickness and 21 mm diameter) placed in glass vial containing 50 ml of NaOH 0.1N at 37° C. under agitation were totally degraded (absence of visible residue) in 10 min.

2. In Aqueous Solvent G#2

Resorbable crosslinker PEG$_{22}$PLGA$_{8}$ (0.33 g, 0.2 mmol) was dissolved in 3 ml distilled water and degased under nitrogen. To this were added poly(ethylene glycol) methyl ether methacrylate Mw 475 (1.9 g, 4 mmol), tetramethylethylenediamine (12 μl) and thioglycolic acid (10 mg). 180 mg of ammonium peroxodisulfate were dissolved in 0.2 ml of distilled water and added to the monomers solution. The mixture was heated at 40° C. for 30 min. After cooling, the polymer was washed with distilled water and freeze-dried.

Hydrogel discs (4 mm thickness and 10 mm diameter) placed in glass vial containing 10 ml of NaOH 0.1N were totally degraded (absence of visible residue) in 10 min.

Example 3: Resorbable Microspheres by Direct Suspension Polymerization

1. Preparation of Resorbable Microspheres

A 0.5% of aqueous solution of 88% hydrolyzed polyvinylalcohol (120 ml) containing 3% NaCl was introduced into a 250 ml reactor and allowed to stand under a nitrogen atmosphere for 15 min. The monomer phase containing poly(ethylene glycol) methyl ether methacrylate, resorbable cross-linker, chain transfer agent (3% mol/mol of PEGMA) and 1 mol % AIBN solubilized in 7.5 ml of toluene was degassed by bubbling nitrogen through the solution for 15 min. The monomer phase was added to the aqueous phase at 80° C. and stirred for 8 h. The mixture was filtered hot and washed with acetone and water. Then, beads were freeze-dried.

A series of resorbable microspheres has been synthesized by varying the nature of crosslinker, and the PEG monomer (Table 2).

TABLE 2

Resorbable Microspheres: Rate of degradation

| | Crosslinker (% mol) | PEGMA (% mol) | MDO (% mol) | Weight loss $^{a,\ b}$ | Mn (kDa)$^c$ |
|---|---|---|---|---|---|
| MS#1 | PEG$_{13}$PLGA$_{12}$ (3%) | DEGMA - 97% | 0 | 23% at 1 month 100% at 4 months | |
| MS#2 | PEG$_{13}$PLGA$_{12}$ (5%) | PEGMA300 - 95% | 0 | 20% at 8 h 80% at 24 h | |
| MS#3 | PEG$_{13}$PLA$_{12}$ (5%) | PEGMA300 - 95% | 0 | 80% at 4 days 100% at 7 days | |
| MS#4 | PEG$_{22}$PLGA$_{12}$ (5%) | PEGMA300 - 95% | 0 | 26% at 8 h 100% at 24 h | 55 |
| MS#5 | PEG$_{22}$PLGA$_{12}$ (5%) | PEGMA300 - 90% | 5 | 100% at 24 h | |
| MS#6 | PEG$_{22}$PLGA$_{12}$ (5%) | PEGMA300 - 85% | 10 | 100% at 24 h | |
| MS#7 | PEG$_{22}$PLGA$_{12}$ (5%) | PEGMA300 - 75% | 20 | 100% at 24 h | 27 |
| MS#8 | PEG$_{22}$PLGA$_{12}$ (5%) | PEGMA300 - 65% | 30 | 100% at 48 h | 15 |

$^a$ PBS, pH7.4 at 37° C.
$^b$ Weight loss (%) = (W0 − Wt)/W0 × 100 where W0 and Wt are the dry weight of the sample before and after degradation, respectively.
$^c$ Molecular weight of polymer chains after degradation The degradation rate of these microspheres can be tailored by varying the chemical composition of crosslinker and/or the nature of the PEG monomer from less than 1 day to up to 4 months. For example, degradation of microspheres containing DEGMA (MS#1) was slower than microspheres made with PEGMA300 (MS#2). Resorbable segments made with PLA (MS#3) slowed down the microsphere degradation compared to crosslinker containing PLGA (MS#2). The length of PEG in resorbable crosslinker modified the fate of microspheres: a faster degradation occurs with PEG22 (MS#4) compared to PEG13 (MS#2).

The cyclic monomer does not notably modify the resorption speed. Moreover, the cyclic monomer reduces the molecular weight of the residual polymer chain after degradation.

2. Control of Size

It is entirely possible to achieve sharp size distributions through a remarkable range of particle sizes by simply varying the stirring speed, the ratio of water to monomer phase, and concentration of polyvinyl alcohol stabilizer. Particle size distribution was determined by laser diffraction on a Mastersizer S apparatus (Malvern Instrument Ltd.) at 25° C. Dry beads were dispersed in water and were allowed to swell for 15 min before measurement. Each injection was analyzed 3 times.

Combination of these factors permits the preparation of size ranges averaging from 220 µm (260 rpm, O/W=1/11), to 317 µm (215 rpm, O/W=1/8), to 614 µm (160 rpm, O/W=1/6) and to 1144 µm (120 rpm, O/W=1/6).

Example 4: Preparation of Resorbable Microspheres by Inverse Suspension Polymerization MS#9

A solution of Span80® (0.2 w %) dissolved in 88 ml of paraffin oil was introduced into a 250 ml reactor and allowed to stand under a nitrogen atmosphere for 15 min. The monomer phase containing poly(ethylene glycol) methyl ether methacrylate Mw475 (4.47 g, 95% mol), $PEG_{22}$-$PLGA_8$ cross-linker (0.86 g, 5% mol), mercaptobutanol (29 µl, 3% mol/mol of PEGMA) and 1 wt % ammonium peroxyde disulfate solubilized in 7.5 ml of water was degassed by bubbling nitrogen through the solution for 15 min. The monomer phase was added to the organic phase at 70° C. and stirred for 2 h. The mixture was filtered hot and washed with water and acetone. Then, beads were freeze-dried.

Example 5: Synthesis of Ionic Resorbable Microspheres

The same procedure by direct suspension polymerization was used as in example 3, but an ionic monomer has been added in the toluene phase (Table 3).

TABLE 3

Ionic Resorbable Microspheres: Rate of degradation

| | Ionic Monomer | Mol % ionic Monomer | Crosslinker[a]/ monomer | MDO (% mol) | Weight loss[b, c] |
|---|---|---|---|---|---|
| MS#10 | β-Carboxy ethyl acrylate | 10 | $PEG_{13}$-$PLGA_{12}$/ PEGMA300 | 0 | 100% at 24 h |
| MS#11 | Methacrylic acid | 10 | $PEG_{13}$-$PLGA_{12}$/ DEGMA | 0 | 98% at 14 days |
| MS#12 | Methacrylic acid | 10 | $PEG_{13}$-$PLA_{12}$/ PEGMA300 | 0 | 100% at 7 days |
| MS#13 | Methacrylic acid | 10 | $PEG_{22}$-$PLA_{12}$/ PEGMA300 | 0 | 100% at 7 days |
| MS#14 | Methacrylic acid | 10 | $PEG_{13}$-$PLGA_{12}$/ PEGMA300 | 0 | 95% at 24 h |
| MS#15 | Methacrylic acid | 20 | $PEG_{13}$-$PLGA_{12}$/ PEGMA300 | 2.5 | 100% at 24 h |
| MS#16 | Methacrylic acid | 50 | $PEG_{22}$-$PLGA_{12}$/ PEGMA300 | 5 | 100% at 12 h |

[a]microspheres prepared with 3 or 5% mol crosslinker
[b]PBS, pH7.4 at 37° C.
[c]Weight loss (%) = (W0 − Wt)/W0 × 100 where W0 and Wt are the dry weight of the sample before and after degradation, respectively.

Microspheres containing various amounts of MDO and different anionic monomers have been synthesised successfully. Their degradation rate in saline buffer was not influenced by the amount of MDO but it was influenced by the amount of ionic monomer, which results from a higher hydrophilic composition of the polymer matrix.

Example 6: Synthesis of Resorbable Hydrogels Containing Cyclodextrins

1. Preparation of Monomethacrylate β-Cyclodextrin

The monomer was synthesized similar to a method previously described (Ren et al. Journal of polymer science, part A 2009, 4267-4278).

Step 1. yield=51%. $^1$H NMR (300 MHz, DMSO-$d_6$): 7.74 (d, 2H, tosyl), 7.45 (d, 2H, tosyl), 4.84-4.77 (m, 7H, O—CH—O), 3.70-3.45 (m, 28H), 3.40-3.20 (m, 14H), 2.43 (s, 3H, Ph-$CH_3$)

Step 2. yield=69% $^1$H NMR (300 MHz, $D_2O$): 9.26 (s, CHO), 5.20-5.10 (m, 7H, O—CH—O), 4.04-3.90 (m, 26H), 3.73-3.60 (m, 14H)

Step 3. yield=71%. $^1$H NMR (300 MHz, $D_2O$): 6.22 (s, =CH), 5.89 (s, =CH), 5.11 (d, 7H, O—CH—O), 4.04-3.88 (m, 28H), 3.71-3.59 (m, 14H), 3.05 (s, 2H, $CH_2$—OCO), 2.90 (s, 2H, $CH_2$—NH), 2.04 (s, 3H, $CH_3$—C=)

2. Preparation of Resorbable Hydrogels with Monomethacrylate β-Cyclodextrin G#3

The monomethacrylate β-cyclodextrin was first solubilised in 4.5 ml of distilled water/DMSO (3/1 vol). To this were added in this order resorbable crosslinker $PEG_{22}$-$PLGA_8$ (0.33 g, 0.2 mmol), poly(ethylene glycol) methyl ether methacrylate Mw 475 (1.71 g, 3.6 mmol), 2-methylene-1,3-dioxepane (0.023 g, 0.2 mmol), tetramethylethylenediamine (12 µl) and thioglycolic acid (10 mg). 180 mg of ammonium peroxodisulfate were dissolved in 0.5 ml of distilled water and added to the monomers solution. The mixture was heated at 40° C. for 30 min. After cooling, the polymer was washed with distilled water and freeze-dried.

Hydrogel discs G#3 (4 mm thickness and 10 mm diameter) placed in glass vial containing 10 ml of NaOH 0.1N were totally degraded (absence of visible residue) in 10 min.

Example 7: Synthesis of Resorbable Hydrogels Containing Crown Ether

1. Preparation of 18-crown-6-methacrylate 2-hydroxymethyl-18-crown-6 (1 mmol) was dissolved in degased $CH_2Cl_2$ (10 mL) in a Schlenk tube equipped with magnetic stirrer. The content of the flask was cooled to 0° C. and triethylamine (3 mmol) was added. The solution was stirred and then methacryloyl chloride (3 mmol) was added dropwise to the solution. The stirring was continued 2H at 0° C. and then overnight at room temperature. The reaction mixture was extracted with 1M HCl solution, washed with water then saturated $Na_2CO_3$ solution and dried over $MgSO_4$. After filtration and evaporation of solvent, the residue was purified by chromatography on silica gel ($CHCl_3$/MeOH 9/1 eluent) to obtain 194 mg (yield 54%) of 2-methylmethacrylate-18-crown-6. $^1$H NMR (300 MHz, $CDCl_3$): 6.11 (s, 1H, =$CH_2$), 5.57 (s, 1H, =$CH_2$), 4.32-4.15 (m, 2H, $CH_2$—OCO), 3.81-3.68 (m, 23H, $CH_2$—O), 1.95 (s, 3H, $CH_3$)

2. Preparation of Resorbable Hydrogels with Crown Ether G#4

Resorbable crosslinker $PEG_{22}$-$PLGA_{12}$ (0.22 g, 0.125 mmol) was dissolved in 0.8 ml toluene and degased under nitrogen. To this were added crown ether methacrylate (0.27 g, 0.75 mmol), poly(ethylene glycol) methyl ether methacrylate Mw 300 (0.49 g, 1.62 mmol), 2-methylene-1,3-dioxepane (14.3 mg, 0.125 mmol) and hexanethiol (7 µl). 2% mol of AIBN were dissolved in 0.2 ml of toluene and added to the monomers solution. The mixture was heated at 80° C. for 8 h. After cooling, the polymer was washed twice with acetone and then distilled water.

Hydrogel discs (4 mm thickness and 10 mm diameter) placed in glass vial containing 10 ml of NaOH 0.1N were totally degraded (absence of visible residue) in 12 h.

Example 8: Synthesis of Resorbable Hydrogels Containing PEI

Resorbable crosslinker $PEG_{22}PLGA_8$ (5% mol) was dissolved in 3 ml distilled water and degased under nitrogen. To this were added polyethylene imine (PEI), poly(ethylene glycol) methyl ether methacrylate Mw 475 (95% mol), tetramethylethylenediamine (7 µl) and thioglycolic acid (12 µl). 1.5% mol of ammonium peroxodisulfate were dissolved in 0.5 ml of distilled water and added to the monomers solution. The mixture was heated at 40° C. for 30 min. After cooling, the polymer was washed with distilled water.

Hydrogel discs (4 mm thickness and 10 mm diameter) placed in glass vial containing 10 ml of NaOH 0.1N were totally degraded (absence of visible residue) in 2 min.

A series of gels has been synthesised with increasing amount of PEI (Table 4).

TABLE 4

Resorbable hydrogels containing PEI

| | Crosslinker $PEG_{22}$-$PLGA_8$ (% mol) | PEG475MA (% mol) | PEI (wt/wt of monomers) |
|---|---|---|---|
| G#5 | 5 | 95 | 1/500 |
| G#6 | 5 | 95 | 1/250 |
| G#7 | 5 | 95 | 1/100 |
| G#8 | 5 | 95 | 1/50 |

Example 9: Synthesis of Resorbable Hydrogels Containing Trypsin

Resorbable crosslinker $PEG_{22}PLGA_8$ (5% mol) was dissolved in 11.5 ml distilled water and degased under nitrogen. To this were added trypsin, poly(ethylene glycol) methyl ether methacrylate Mw 475 (95% mol), tetramethylethylenediamine (30 µl) and thioglycolic acid (26 mg). 1.5% mol of ammonium peroxodisulfate were dissolved in 0.5 ml of distilled water and added to the monomers solution. The mixture was heated at 40° C. for 30 min. After cooling, the polymer was washed with distilled water.

Hydrogel discs (4 mm thickness and 10 mm diameter) placed in glass vial containing 10 ml of NaOH 0.1N were totally degraded (absence of visible residue) in 2 min.

A series of gels have been synthesised with increasing amount of trypsin (Table 5).

TABLE 5

Resorbable hydrogels containing trypsin

| | Crosslinker $PEG_{22}$-$PLGA_8$ (% mol) | PEG475MA (% mol) | Trypsin (mg) |
|---|---|---|---|
| G#9 | 5 | 95 | 0 |
| G#10 | 5 | 95 | 5 |
| G#11 | 5 | 95 | 10 |

Example 10: Synthesis of Resorbable Hydrogels Containing bFGF

Resorbable crosslinker $PEG_{22}PLGA_8$ (5% mol) was dissolved in 14 ml distilled water and degased under nitrogen. To this were added bFGF, poly(ethylene glycol) methyl ether methacrylate Mw 475 (95% mol), tetramethylethylenediamine (30 µl) and thioglycolic acid (30 mg). 1.5% mol of ammonium peroxodisulfate were dissolved in 0.5 ml of distilled water and added to the monomers solution. The mixture was heated at 40° C. for 30 min. After cooling, the polymer was washed with distilled water.

Hydrogel discs (4 mm thickness and 10 mm diameter) placed in glass vial containing 10 ml of NaOH 0.1N were totally degraded (absence of visible residue) in 10 min.

A series of gels have been synthesised with increasing amount of bFGF (Table 6).

TABLE 6

Resorbable hydrogels containing bFGF

| | Crosslinker $PEG_{22}$-$PLGA_8$ (% mol) | PEG475MA (% mol) | bFGF (µg) |
|---|---|---|---|
| G#12 | 5 | 95 | 10 |
| G#13 | 5 | 95 | 50 |
| G#14 | 5 | 95 | 100 |

Example 11: Loading of Avastin® on Resorbable Microspheres

Bevacizumab (Avastin®) is a humanized monoclonal IgG antibody, the apparent isoelectric point (pI) values of the respective isoforms are 8.26, 8.45, and 8.59 (Vlckova et al., 2008 J. Chromatogr. A, 1181: 145-152). At pH 7, the antibody is positively charged and could be immobilized on anionic microspheres.

1—Loading of Antibody

In water, 100 µL of sterilized microspheres described in examples 3 and 5 (100-300 µm) were mixed with 1 mL of water at pH 7 before addition of antibody solution (Avastin® 25 mg/mL, Roche). After mixing, the test tubes were incubated horizontally at 37° C. under agitation for 1 h. The residual antibody in water was determined using the bicinchoninic acid method (BCA protein Reagent, Sigma) with BSA as protein standard (Table 7).

TABLE 7

Percentage of antibody loading obtained at pH 7 with 100 μL of microsphere pellets in 1 mL of medium

|  | MS#3 | MS#12 | MS#2 | MS#14 | Microsphere control* |
|---|---|---|---|---|---|
| Nature of microspheres | PLA | PLA | PLGA | PLGA |  |
| % MA | 0 | 10 | 0 | 10 | — |
| Avastin ® (300 μg) | 5 | 100 | 12 | 100 | 92 |
| Avastin ® (600 μg) | 0.6 | 97 | 9 | 100 | 100 |
| Avastin ® (1300 μg) | 0.3 | 45 | 0 | 100 | 100 |

*HepaSphere ™/QuadraSphere ™ (BioSphere Medical)

Antibody binding occurred on microspheres containing methacrylic acid (MS#12 and 14) suggesting that electrostatic bonds are formed between positively charged antibody and carboxylic acid functions of anionic MS. On contrary, very low or no antibody immobilisation was observed with MS containing no methacrylic acid (MS#2 and 3). Ionic binding of bevacizumab to anionic microspheres was demonstrated with gold standard embolization particles, HepaSphere™/QuadraSphere™. Interestingly, resorbable anionic microspheres built with PLGA resorbable crosslinkers seem to be more efficient for immobilization of bevacizumab.

2—Assessment of Antibody Release from Microspheres

The loading medium was removed, and was replaced with the same volume of phosphate saline buffer. Pellets were mixed and medium were removed at regular intervals and they were replaced with fresh PBS. Antibody release was performed at 37° C. under shaking. The amount of bevacizumab released in medium was determined using the BCA method. After incubation (1 h at 37° C.), absorbance was measured at 550-570 nm and the amount of free antibody was obtained by extrapolation from standard curve using bovine serum albumin (Table 8).

TABLE 8

Bevacizumab release in saline buffer (37° C.). Amount of proteins measured in release medium for loading of Avastin ® (1300 μg proteins) performed on 100 μL of microsphere pellets.

|  | MS#12 | MS#14 | Microsphere control* |
|---|---|---|---|
| Nature of microspheres | PLA | PLGA | — |
| % MA | 10 | 10 | — |
| 5 min in PBS (μg proteins) | 5.4 | 39.7 | 571.5 |
| 1 h in PBS (μg proteins) | 179.2 | 348.2 | 329.4 |
| 2 h in PBS (μg proteins) | 80.7 | 168 | 31.6 |
| 4 h in PBS (μg proteins) | 89.6 | 204 | 0 |
| 24 h in PBS (μg proteins) | 192.7 | 164.8 | 0 |
| 48 h in PBS (μg proteins) | 48.2 | 70.3 | 0 |
| Total amount of released antibody (μg) (% of initial charge) | 595 (100%) | 995 (81%) | 932 (70%) |

*HepaSphere ™/QuadraSphere ™ (BioSphere Medical)

A sustained release of bevacizumab from anionic resorbable microspheres occurred during 48 h of incubation in PBS without initial burst. On contrary, a burst of antibody release was observed for the gold standard chemioembolization product, HepaSphere™/QuadraSphere™, which released around 70% of the initial dose of immobilized antibody on the first hour.

3—In Vitro Activity of Released Antibody: Inhibition of HUVEC Proliferation

Human umbilical endothelial cells (HUVEC) were seeded into 96 well-plates (Nunc) at a density of 5000 cells per well in complete EGM-2 medium (Lonza) with all cell culture supplements. The day after seeding, the released fractions collected during in vitro release experiments were mixed with EBM-2 medium containing 50 ng/mL of mouse VEGF (R&D) and HUVEC cells were cultured for 3 days until analysis of cell lysis. The amount of released bevacizumab added to cell was 100 and 500 ng/mL. As positive control, cells were treated with Avastin® dilutions. Cell lysis was determined by measuring the lactate dehydrogenase activity optical density (OD) (Promega) in cell culture medium at the end of culture (Table 9).

TABLE 9

In vitro efficacy of released fractions collected from resorbable microsphere loaded with bevacizumab. Neutralisation of VEGF with bevacizumab increased HUVEC lysis

|  | | | | | MS#12 | | | |
|---|---|---|---|---|---|---|---|---|
|  | | | | | 100 ng/mL | | 500 ng/mL | |
|  | Free Avastin (ng/mL) | | | | 1 h of release | 24 h of release | 1 h of release | 24 h of release |
|  | Control 0 | 100 | 500 | 1 000 | | | | |
| LDH activity in cell culture medium (OD 450 nm) | 0.203 ± 0.011 | 0.191 ± 0.024 | 0.286 ± 0.055 | 0.417 ± 0.065 | 0.204 ± 0.019 | 0.197 ± 0.028 | 0.331 ± 0.055 | 0.305 ± 0.064 |
| $p^a$ | | NS | 0.0039 | 0.0039 | NS | NS | 0.0039 | 0.0039 |
| $p^b$ | | | | | | | NS | NS |
| $p^c$ | | | | | | | 0.0370 | 0.0370 |

TABLE 9-continued

In vitro efficacy of released fractions collected from resorbable microsphere loaded with bevacizumab. Neutralisation of VEGF with bevacizumab increased HUVEC lysis

| | Free Avastin (ng/mL) | | | | MS#14 | | | |
|---|---|---|---|---|---|---|---|---|
| | | | | | 100 ng/mL | | 500 ng/mL | |
| | Control 0 | 100 | 500 | 1 000 | 1 h of release | 24 h of release | 1 h of release | 24 h of release |
| LDH activity in cell culture medium (OD 450 nm) | 0.203 ± 0.011 | 0.191 ± 0.024 | 0.286 ± 0.055 | 0.417 ± 0.065 | 0.215 ± 0.024 | 0.191 ± 0.024 | 0.38 ± 0.104 | 0.412 ± 0.084 |
| $p^a$ | | NS | 0.0039 | 0.0039 | NS | NS | 0.0039 | 0.0039 |
| $p^b$ | | | | | | | NS | 0.0104 |
| $p^c$ | | | | | | | NS | NS |

$^a$Comparisons between control (no bevacizumab) and bevacizumab treatments (free Avastin ® and release fractions) were performed according to non-parametric Mann-Whitney test. Significance was set at p < 0.05. NS: non-significant
$^b$Comparisons between 500 ng of released antibody (1 h and 24 h) and free bevacizumab at 500 ng/mL (non-parametric Mann-Whitney test, Significance was set at p < 0.05).
$^c$Comparisons between 500 ng of released antibody (1 h and 24 h) and free bevacizumab at 1000 ng/mL (non-parametric Mann-Whitney test, Significance was set at p < 0.05).

During our cell-based assay, control bevacizumab (Avastin® 25 mg/mL, Roche) at 0.5 and 1 µg/mL increased (p<0.05) the release of intracellular lactate dehydrogenase in cell culture medium which indicates cell death events.

An increase of lactate dehydrogenase leakage from HUVEC was significantly observed (p<0.05) with fractions collected after 1 h and 24 h of incubation of ionic resorbable MS#12 and #14 in PBS compared to control without antibody treatment. The released antibody from MS#12 (500 ng/mL) reduced cell viability as measured with the same dose of Avastin® control. Antibody released from MS#14 was equivalent to the biological activity induced with 1 µg/mL of control antibody.

These results indicate that the biological activity of eluted bevacizumab from degradable microspheres was preserved. In conclusion, resorbable ionic microspheres release functional non-denatured bevacizumab antibody.

Example 12: bFGF Loading on Microspheres

1—Cytokine Loading

Water was removed by aspiration from 100 µL of sterilized microspheres (100-300 µm) previously hydrated. The freeze-dried human recombinant basic fibroblast growth factor (rh-bFGF) (Fiblast, Trafermin, Kaken Pharmaceutical Co., Inc (Tokyo, Japan)) was dissolved in sterile water adjusted at pH7 (0.33 µg bFGF/µL). To microsphere pellets, 50 µL of Fiblast solution were added, and after mild mixing by inversion, the cytokine binding to particles was achieved overnight at 4° C. (Table 10).

TABLE 10

Fiblast loading (in % of initial dose) obtained at pH 7 (4° C., overnight) with 100 µL of microsphere pellets

| | MS#3 | MS#12 | MS#2 | MS#14 | DCBeads 700-900 µm |
|---|---|---|---|---|---|
| Nature of microspheres | PLA | PLA | PLGA | PLGA | — |
| % MA | 0 | 10 | 0 | 10 | — |
| % of Fiblast Loading | 75 | 49 | 66 | 23 | 88 |

TABLE 10-continued

Fiblast loading (in % of initial dose) obtained at pH 7 (4° C., overnight) with 100 µL of microsphere pellets

| | MS#3 | MS#12 | MS#2 | MS#14 | DCBeads 700-900 µm |
|---|---|---|---|---|---|
| Amount of immobilized cytokine (µg) | 12.3 | 8 | 10.9 | 3.8 | 14.5 |

Cytokine loading on anionic resorbable microspheres is effective as obtained with anionic gold standard DC beads. The binding to resorbable microspheres without methacrylic acid seems more efficient (MS#3 and MS#2) than observed with microspheres containing methacrylic acid (MS#12 and MS#14). Strong basic proteins (pI close to 10) probably interact strongly with some negatively charges of polymer matrix of resorbable microspheres without the need of methacrylic acid.

2—Assessment of bFGF Release from Microspheres

Phosphate buffer saline (200 µL) was added to microsphere pellets and medium was removed at regular intervals and was replaced with fresh PBS. Cytokine release was performed at 37° C. under shaking. Supernatant removal was performed at 5 min, 1 h, 24 h and 48 h. The amount of bFGF released in medium was determined using the BCA method. After incubation (1 h at 37° C.), absorbance was measured at 550-570 nm and the amount of free cytokine was obtained by extrapolation from standard curve using bovine serum albumin (Table 11). Blank microspheres were treated in the same way without bFGF in order to assess substances released from microspheres which could interfere with BCA assay.

TABLE 11

Fiblast release in PBS at 37° C. The amount of proteins was detected in release medium according to BCA assay.

| | MS#3 | MS#12 | MS#2 | MS#14 | DCBeads 700-900 µm |
|---|---|---|---|---|---|
| Nature of microspheres | PLA | PLA | PLGA | PLGA | — |
| % MA | 0 | 10 | 0 | 10 | — |

TABLE 11-continued

Fiblast release in PBS at 37° C. The amount of proteins was detected in release medium according to BCA assay.

|  | MS#3 | MS#12 | MS#2 | MS#14 | DCBeads 700-900 μm |
|---|---|---|---|---|---|
| 5 min of release (μg proteins) | 0.7 | 4.2 | 6.2 | 1.36 | 3.1 |
| 1 h of release (μg proteins) | 0.04 | 0.6 | 1.1 | 0.12 | 1.3 |
| 24 h of release (μg proteins) | 1.2 | 1 | 0.95 | 0 | 0.8 |
| 48 h of release (μg proteins) | 1.2 | 1.3 | 0.7 | 0.7 | 1.1 |
| Total amount of released cytokine (μg) (% of initial charge) | 3.1 (25%) | 7.1 (87%) | 8.9 (82%) | 2.1 (57%) | 6.3 (43%) |

A sustained release of bFGF was measured for each microsphere, ionic and non-ionic resorbable microspheres. The amount (in μg) of bFGF released from MS#12 and MS#2 was similar to the elution achieved for DCbeads.

3—In Vitro Activity of Released Cytokine

Human umbilical endothelial cells (HUVEC) were seeded into 96 well-plates (Nunc) at a density of 5000 cells per well in complete EGM-2 medium (Lonza) with all cell culture supplements. The day after seeding, fractions collected during in vitro release experiments were mixed with EBM-2 medium without any cytokines (5 to 8 wells per condition). HUVEC were cultured for 4 days until analysis of cell proliferation. As positive control of cell proliferation, cells were treated with Fiblast solution (100 ng bFGF/mL). Cell proliferation was determined by measuring the total cell protein using BCA assay (Table 12).

from the blank microspheres (without bFGF loading). Cell proliferation induced with bFGF eluted from MS#12 (1 h, 24 h and 48 h) was equivalent to cell response observed during culture with the Fiblast control (100 ng/m L).

On contrary, in fractions collected from DC beads loaded with bFGF, no significant ($p>0.05$) induction of cell proliferation was measured (5 min, 1 h, 24 h) as observed upon comparison with cell culture control and Blank microspheres. A low proliferative activity was observed with the last collected fraction (48 h), which is significantly lower than the proliferation induced with the Fiblast control solution (100 ng/m L).

In conclusion, bFGF adsorbed onto degradable microspheres keeps its biological activity which is not the case for DC beads despite a better bFGF immobilization.

Example 13: Polyplexes Loading on Microspheres

1—Polyplexes Formation

DNA was condensed with branched polyethylenimine (PEI) of 25 kDa at a molar ratio of PEI nitrogen to DNA phosphate (N/P ratio) of 5. DNA/PEI polyplexes were prepared at a final DNA concentration of 400 μg/mL by flash-mixing of linear salmon sperm DNA (Sigma) with PEI in water containing 5% glucose. Polyplexes were allowed to stand for at least 20 min at room temperature before use.

2—Microspheres (100-300 μm) Loading with Polyplexes

In water, 100 μL of sterilized microsphere pellets were mixed with polyplexes solution. After mild mixing, the test tubes were incubated horizontally in an oven at 37° C. under agitation for 1 h. The polyplexes binding onto microspheres was quantified by measuring the absorbance supernatant at 260 nm. As control, blank microspheres were treated in the same way without DNA (Table 13).

TABLE 12

In vitro efficacy of released Fiblast collected from resorbable microspheres (MS#12) and non-resorbable DC beads. After 4 days of culture, proliferation of HUVEC was determined according to total proteins assay.

|  | Period of release | Fiblast loaded microsphere | | | | Blank microsphere | | | | Cell culture control | Fiblast control solution (100 ng/mL) |
|---|---|---|---|---|---|---|---|---|---|---|---|
|  |  | 5 min | 1 h | 24 h | 48 h | 5 min | 1 h | 24 h | 48 h |  |  |
| MS#12 | Total cell proteins (μg) | 4.67 ± 1 | 7.12 ± 0.9 | 7.91 ± 0.36 | 8.43 ± 1 | 5.23 ± 0.96 | 4.87 ± 0.76 | 5.05 ± 0.78 | 5.86 ± 0.95 | 4.69 ± 0.65 | 7.67 ± 0.77 |
|  | $p^a$ | 0.9585 | 0.0039 | 0.0019 | 0.0019 |  |  |  |  |  | 0.0062 |
|  | $p^b$ | 0.4008 | 0.0027 | 0.0008 | 0.0143 |  |  |  |  |  |  |
|  | $p^c$ | 0.0034 | 0.5642 | 0.2416 | 0.1432 |  |  |  |  |  |  |
| DC-Beads | Total cell proteins (μg) | 4.32 ± 1 | 3.32 ± 0.34 | 4.19 ± 1.5 | 5.16 ± 0.22 | 3.58 ± 0.39 | 3.59 ± 0.35 | 3.10 ± 0.24 | 3.41 ± 0.3 | 3.3 ± 0.35 | 6.48 ± 0.52 |
|  | $p^a$ | 0.0609 | 0.6973 | 0.6056 | 0.0201 |  |  |  |  |  | 0.0062 |
|  | $p^b$ | 0.0585 | 0.1146 | 0.1031 | 0.0339 |  |  |  |  |  |  |
|  | $p^c$ | 0.0043 | 0.0033 | 0.0281 | 0.0253 |  |  |  |  |  |  |

[a] Comparison between Fiblast treatments (Fiblast loaded microspheres and Fiblast control solution) and cell culture control was performed according to non-parametric Mann-Whitney test. Significance was set at $p < 0.05$
[b] Comparison between Fiblast eluded from microspheres to Blank microspheres at each time of sampling (Mann-Whitney test, Significance was set at $p < 0.05$)
[c] Comparison between Fiblast eluted from microspheres to control Fiblast solution (100 ng/mL) (Mann-Whitney test, Significance was set at $p < 0.05$)

When HUVEC were cultured with dilutions of release fractions (1 h, 24 h and 48 h) obtained from MS#12 previously loaded with bFGF, cell proliferation was significantly ($p<0.05$) improved from the first hour compared to cell culture control (without Fiblast) and fractions recovered 3—Assessment of Polyplexes Release from Microspheres The loading medium was discarded and phosphate saline buffer (200 μL) were added to microspheres. DNA release was performed at 37° C. under shaking, PBS medium was removed at 5 min, 1 h and 24 h. The amount of DNA release was determined by measuring the absorbance at 260 nm (Table 13).

TABLE 13

Polyplexes loading on resorbable microspheres and release

|  | MS#3 | MS#12 | MS#2 | MS#14 | DCBeads 700-900 µm |
|---|---|---|---|---|---|
| Nature of microspheres | PLA | PLA | PLGA | PLGA | — |
| % MA | 0 | 10 | 0 | 10 | — |
| µg of DNA loaded on microspheres at 1 h | 200 | 214 | 212 | 232 | 31 |
| % DNA loading (1 h) | 76 | 77 | 77 | 78 | 11 |
| DNA release at 5 min (µg) | 34 | 44 | 62 | 118 | 26 |
| DNA release at 1 h (µg) | 20 | 46 | 45 | 42 | 6 |
| DNA release at 24 h (µg) | 8 | 10 | 11 | 7 | 0 |
| Total amount of released DNA (µg) | 62 (31% of initial charge) | 100 (46% of initial charge) | 118 (55% of initial charge) | 167 (71% of initial charge) | 32 (100% of initial charge) |

A low polyplexes binding to DC Beads was observed, while polyplexes loading onto resorbable microspheres was higher (6-fold). Polyplexes loading seems independent of the particle charge, the loading occurred onto ionic degradable microspheres containing methacrylic acid (MS#12 and MS#14), and onto microspheres without methacrylic acid (MS#3 and MS#2).

The DNA release from DC beads occurred according to a burst profile, while a sustained release of DNA was measured with resorbable microspheres. The release seemed more rapid with anionic resorbable microspheres containing PLGA crosslinker. For the other resorbable microspheres, around half of loaded-DNA was eluted during 24 h of incubation in saline buffer. These particles could be efficient carriers for local delivery of DNA.

Example 14: Degradable Gels Containing Branched 25 kDa Polyethyleneimine for DNA Adsorption 1—Gel Loading with DNA Using a biopsy punch, 6 mm diameter plugs were prepared from gels containing various amounts of PEI. Wet gel plugs (around 100 mg) were washed with water until the absorbance at 260 nm was close to zero. One mL of sperm salmon linear DNA (125 µg in 1 mL of water) was added to washed-gel plugs (in duplicate). DNA loading was performed at 37° C. under shaking and DNA adsorption was monitored by measuring the absorbance of supernatant at 260 nm after 2 h of incubation.

2—Assessment of DNA Release from Microspheres

To gel plugs, 1 mL of phosphate saline buffer was added and incubation occurred at 37° C. under shaking. DNA release was determined by measuring the absorbance of medium at 260 nm. As control, unloaded DNA gel plugs were treated in the same conditions to determine the release of substances from gels which interfere with DNA measure at 260 nm (Table 14).

TABLE 14

DNA loading on resorbable gels containing polyethyleneimine and DNA release attempts.

|  | G#6 | G#7 | G#2 |
|---|---|---|---|
| PEI/PEG475ma (w/w) | 1/250 | 1/100 | 0 |
| DNA loading at 2 h (µg) | 88 | 116 | 5 |
| % of DNA loading (2 h) | 70 | 92 | 4 |
| DNA release (µg) in PBS (30 min) | 48 | 1.5 | 5 |
| DNA release (µg) in PBS (24 h) | 5 | 2.5 | 0 |
| Total amount of released DNA (µg) | 53 (75% of initial charge) | 4 (4% of initial charge) | 5 (100% of initial charge) |

A good DNA immobilization efficiency was achieved with gels containing PEI (G#6 and G#7) compared to gel without PEI (G#2).

Release experiments in neutral saline buffer show a burst for the gel containing the lower PEI concentration (G#6) while a more sustained DNA release was achieved with gel containing more PEI (1%, w/w) (G#7).

The rapid burst observed with G#6 may correspond to elution of DNA bound to gel via electrostatic interactions, while on gel containing more PEI (G#7), DNA compaction with PEI leading to formation of polyplexes had probably occurred. Release of polyplexes was probably slower than elution of naked DNA. In conclusion, by varying the concentration of PEI in resorbable gels, different patterns for DNA release could be obtained.

Example 15: Non-Denaturing Incorporation of Proteins in Degradable Gels. Bovine Trypsin as Model Protein Assessment of Trypsin Release from Degradable Gels Using a biopsy punch, 6 mm diameter plugs (200-300 mg) were prepared from gels. To wet gel plugs (in duplicate), 1 mL of PBS (10 mM phosphate buffer, 0.9% NaCl, pH 7.2) was added and incubation occurred at 37° C. under shaking. Trypsin activity was determined by addition of 80 µL of trypsin synthetic substrate (1 mM benzoyl-DL-arginine 4-nitroanilide hydrochloride in 50 mM sodium bicarbonate) to 20 µL of PBS medium removed after 5 min 1 h, 3 h and 24 h of incubation. Trypsin activity in release medium was measured at 405 nm after one hour of incubation at 37° C. Trypsin activity in release medium (OD 405 nm) was normalized with the mass of wet gel (OD405 nm for 100 mg of gel) (Table 15).

TABLE 15

Release of active protein from degradable hydrogel during incubation in saline buffer

| Trypsin (mg/g gel) | Trypsin activity (OD405 nm for 100 mg of gel) measured in PBS during release experiments | | | |
|---|---|---|---|---|
|  | 5 min | 1 h | 3 h | 24 h |
| G#10  0.9 | 0.11 ± 0.006 | 0.22 ± 0.014 | 0.21 ± 0.009 | 0.042 ± 0.003 |
| G#11  1.8 | 0.27 ± 0.019 | 0.34 ± 0.03 | 0.303 ± 0.029 | 0.096 ± 0.014 |

TABLE 15-continued

Release of active protein from degradable hydrogel during incubation in saline buffer

| Trypsin (mg/g gel) | Trypsin activity (OD405 nm for 100 mg of gel) measured in PBS during release experiments | | | |
|---|---|---|---|---|
| | 5 min | 1 h | 3 h | 24 h |
| | (p = 0.202)* | (p = 0.029) | (p = 0.0209) | (p = 0.0209) |

*Comparisons between G#11 and G#10 were performed according to non-parametric Mann-Whitney test. (Significance was set at p < 0.05).

Incubation of resorbable gels containing trypsin in buffer leads to the release of active trypsin molecules up to 24 h. The trypsin release in medium was proportional to the amount of enzyme incorporated in the gels. The measurement of enzymatic activity at the different sampling times (5 min, 1 h, 3 h, 24 h) showed that preparation of trypsin loaded resorbable gels is achievable and that loading does not inactivate the proteins.

Example 16: In Vitro Cytotoxicity Analysis (Table 16)

Cytotoxicity of microspheres was analyzed using extracts of microspheres prepared in cell culture medium. Briefly, mouse fibroblasts (L929) cultures were maintained in high-glucose DMEM medium with 10% FBS, 2 mM L-glutamine, 50 µg/mL streptomycin, 50 Units/mL penicillin in $CO_2$ incubator at 37° C. L929 cells harvesting was performed using Trypsin EDTA (Lonza) and subcultures started in 96 well plates (NUNC) at densities of $5.10^3$ cells/well. Microspheres extracts were prepared in sterile tubes, 500 µL of microspheres pellet in DMEM were added and the volume was completed to 3 mL with cell culture medium. Samples were incubated at 37° C. under agitation up to complete degradation of microspheres. The concentration of material was around 25 mg/mL in the microsphere extracts. Chirurgical glove fragments (latex) were used as positive control of cytotoxicity. The day after cell seeding, the microspheres extracts in cell culture medium were completed with bovine serum and the pH was adjusted (around pH 7) before addition to non-confluent fibroblasts (6 to 8 wells/condition). Extracts obtained with chirurgical gloves were also added to mouse fibroblasts. After 72 h of culture (37° C., 5% $CO_2$), medium was removed, cells were washed with 100 µL of PBS, before addition of 100 µL bicinchoninic acid solution (BCA protein Reagent, Sigma) containing 0.08% CuSO4 (w/v) and 0.05% Triton X-100. After incubation (1 h at 37° C.), absorbance was measured at 570 nm and the amount of proteins was obtained by extrapolation from standard curve using bovine serum albumin (Table 16).

TABLE 16

Cytotoxicity of resorbable microspheres

| Code | Crosslinker (% mol) | MDO (% mol) | Co-Monomer (% mol) | L929 total cell proteins (% of control) | Cytotoxic status |
|---|---|---|---|---|---|
| Cell culture medium (Non-Cytotoxic Control) | — | — | — | 100 | Non-cytotoxic |
| Latex (Cytotoxic control) | — | — | — | 22.73 +/− 5.74 | Cytotoxic |
| MS#2 | $PEG_{13}PLGA_{12}$ (5%) | 0 | — | 71.36 +/− 6.14 * p = 0.0003 | Non-cytotoxic |
| MS#3 | $PEG_{13}PLA_{12}$ (5%) | 0 | — | 83.80 +/− 3.99 * p = 0.0003 | Non-cytotoxic |
| MS#4 | $PEG_{22}PLGA_{12}$ (5%) | 0 | — | 85.09 +/− 4.5 * p = 0.0003 | Non-cytotoxic |
| MS#10 | $PEG_{13}$-$PLGA_{12}$ (5%) | 0 | β-Carboxy ethyl acrylate (10%) | 61.59 +/− 7.7 * p = 0.0008 | Mildly cytotoxic |
| MS#12 | $PEG_{13}$-$PLA_{12}$ (5%) | 0 | Methacrylic acid (10%) | 74.94 +/− 7.04 * p = 0.0003 | Non-cytotoxic |
| MS#14 | $PEG_{13}$-$PLGA_{12}$ (5%) | 0 | Methacrylic acid (10%) | 72.34 +/− 4.26 * p = 0.0003 | Non-cytotoxic |
| MS#5 | $PEG_{22}PLGA_{12}$ (5%) | 5 | — | 86.31 +/− 4.44 * p = 0.0039 | Non-cytotoxic |
| MS#6 | $PEG_{22}PLGA_{12}$ (5%) | 10 | — | 88.46 +/− 7.67 * p = 0.0007 | Non-cytotoxic |
| MS#8 | $PEG_{22}PLGA_{12}$ (5%) | 30 | — | 73.65 +/− 5.16 * p = 0.0039 | Non-cytotoxic |
| MS#16 | $PEG_{22}$-$PLGA_{12}$/ | 5 | Methacrylic acid (50%) | 22.79 +/− 3.32 * p = 0.0039 | Cytotoxic |

*: comparison between microsphere and Latex (non-parametric Mann-Whitney test). Significance was set at p <0.05.

Significant cytotoxicity was defined as an effect leading to an inhibition of cell growth of more than 30% as compared to the control cultures (Lin et al 2009 Colloid Surface B, 70: 132-41).

Addition of 2-methylene-1,3-dioxepane (MDO) within the polymer matrix (from 5 up to 30%) did not induce cytotoxicity during the culture period. In conclusion, addition of MDO in microspheres reduces the molecular weight of the degradation products without induction of cytotoxicity.

Methacrylic acid at 10% mol (MS#12 and MS#14) in resorbable microspheres was not cytotoxic in comparison with microspheres prepared without methacrylic acid (MS#3 and MS#2). At the opposite, incorporation of a high content of methacrylic acid (50% mol) within microsphere (MS#16) generated toxicity, attributable to a quick resorption giving a high release of protons (pH dropped below 7) which compromised the cell survival.

Addition of β-Carboxy-ethyl acrylate (10% mol) in microspheres (MS#10) induced a limited toxicity; the growth inhibition was close to the threshold value for cytotoxicity (70%). Methacrylic acid seems to be a better anionic co-monomer compared to β-carboxy-ethyl acrylate for preparation of anionic microspheres in regard to the toxicity results.

Except for MS#10 and MS#16, the cell proliferation values obtained with the resorbable microspheres listed in table 12 were higher than 70%, thus they are considered as non-cytotoxic towards cultured cells.

The invention claimed is:

1. A macromolecule-loaded bioresorbable crosslinked polymer wherein the polymer is obtainable from the polymerization of:
    (i) at least one monomer of formula (I)

$$(CH_2=CR_1)CO—K \qquad (I)$$

wherein:
    K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
    $R_1$, $R_2$, $R_3$, $R_4$ and $R_5$ independently represent H or a $C_1$-$C_6$ alkyl;
    and
    (ii) at least one bio-resorbable block copolymer cross-linker, wherein the bio-resorbable block copolymer cross-linker is linear and selected from the group consisting of polyethylene glycol (PEG), poly-lactic acid (PLA), poly-glycolic acid (PGA), poly-lactic-glycolic acid (PLGA) and poly(caprolactone) (PCL); and is of the following formula (II):

$$(CH_2=CR_7)CO—(X_n)_j—PEG_p-Y_k—CO—(CR_8=CH_2) \qquad (II)$$

wherein:
    $R_7$ and $R_8$ independently represent H or a $C_1$-$C_6$ alkyl;
    X and Y independently represent PLA, PGA, PLGA or PCL;
    n, p, and k respectively represent the degree of polymerization of X, PEG, and Y, n and k independently being integers from 1 to 150, and p being an integer from 1 to 100;
    j represents 0 or 1; and
    (iii) at least one chain transfer agent, wherein the at least one chain transfer agent is a cycloaliphatic or an aliphatic thiol having from 2 to 24 carbon atoms,
    and wherein the loaded macromolecule is selected from the group consisting of proteins and nucleic acids.

2. The polymer of claim 1, wherein the bio-resorbable block copolymer cross-linker is of a formula selected from the group consisting of:
    $(CH_2=CR_7)CO$-$PLA_n$-$PEG_p$-$PLA_k$-$CO$— $(CR_8=CH_2)$,
    $(CH_2=CR_7)CO$-$PGA_n$-$PEG_p$-$PGA_k$-$CO$— $(CR_8=CH_2)$,
    $(CH_2=CR_7)CO$-$PLGA_n$-$PEG_p$-$PLGA_k$-$CO$— $(CR_8=CH_2)$,
    $(CH_2=CR_7)CO$-$PEG_p$-$PLA_k$-$CO$— $(CR_8=CH_2)$,
    $(CH_2=CR_7)CO$-$PEG_p$-$PGA_k$-$CO$— $(CR_8=CH_2)$, and
    $(CH_2=CR_7)CO$-$PEG_p$-$PLGA_k$-$CO$— $(CR_8=CH_2)$;
    wherein $R_7$, $R_8$, n, p and k are as defined in claim 1.

3. The polymer of claim 1, wherein the monomer of formula (I) is selected from the group consisting of sec-butyl acrylate, n-butyl acrylate, t-butyl acrylate, t-butyl methacrylate, methylmethacrylate, N-dimethyl-aminoethyl(methyl) acrylate, N,N-dimethylaminopropyl-(meth)acrylate, t-butylaminoethyl (methyl) acrylate, N,N-diethylaminoacrylate, acrylate terminated poly(ethylene oxide), methacrylate terminated poly(ethylene oxide), methoxy poly(ethylene oxide) methacrylate, butoxy poly(ethylene oxide) methacrylate, acrylate terminated poly(ethylene glycol), methacrylate terminated poly(ethylene glycol), methoxy poly(ethylene glycol) methacrylate, butoxy poly(ethylene glycol) methacrylate, and poly(ethylene glycol) methyl ether methacrylate.

4. A macromolecule-loaded bioresorbable crosslinked polymer wherein the polymer is obtainable from the polymerization of:
    (i) at least one monomer of formula (I)

$$(CH_2=CR_1)CO—K \qquad (I)$$

wherein:
    K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
    $R_1$, $R_2$, $R_3$, $R_4$ and $R_5$ independently represent H or a $C_1$-$C_6$ alkyl;
    (ii) at least one bio-resorbable block copolymer cross-linker, wherein the bio-resorbable block copolymer cross-linker is linear and presents $(CH_2=(CR_6))$— groups at both its extremities, wherein $R_6$ independently represents H or a $C_1$-$C_6$ alkyl;
    (iii) at least one chain transfer agent, wherein the at least one chain transfer agent is a cycloaliphatic or an aliphatic thiol having from 2 to 24 carbon atoms, and
    (iv) further at least one cyclic monomer having an exomethylene group of formula (III):

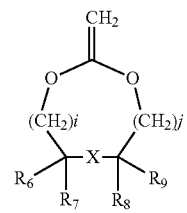

wherein:
    $R_6$, $R_7$, $R_8$ and $R_9$ represent independently H or a $C_5$-$C_7$ aryl group or $R_7$ and $R_8$ are absent and $R_7$ and $R_8$ form
    together with the carbon atom on which they are bonded a $C_5$-$C_7$ aryl group;
    i and j represent independently an integer from 0 to 2; and
    X represents either O or X is not present and in this latter case, $CR_6R_7$ and $CR_8R_9$ are linked via a single bond C—C; and
    wherein the loaded macromolecule is selected from the group consisting of proteins and nucleic acids.

5. The polymer of claim 4, wherein the at least cyclic monomer of formula
    (III) is selected from the group consisting of 2-methylene-1,3-dioxolane, 2-methylene-1,3-dioxane, 2-methylene-4-phenyl-1,3-dioxolane, 2-methylene-1,3-dioxepane, 5,6-benzo-2-methylene-1,3dioxepane and 2-methylene-1,3,6-trioxocane.

6. A macromolecule-loaded bioresorbable crosslinked polymer wherein the polymer is obtainable from the polymerization of:
(i) at least one monomer of formula (I)

$(CH_2=CR_1)CO—K$ (I)

wherein:
K represents O—Z or NH—Z, Z representing $(CR_2R_3)_m—CH_3$, $(CH_2—CH_2—O)_m—H$, $(CH_2—CH_2—O)_m—CH_3$, $(CH_2)_m—NR_4R_5$ with m representing an integer from 1 to 30;
$R_1$, $R_2$, $R_3$, $R_4$ and $R_5$ independently represent H or a $C_1$-$C_6$ alkyl;
(ii) at least one bio-resorbable block copolymer cross-linker, wherein the bio-resorbable block copolymer cross-linker is linear and presents $(CH_2=(CR_6))$— groups at both its extremities, wherein $R_6$ independently represents H or a $C_1$-$C_6$ alkyl;
(iii) at least one chain transfer agent, wherein the at least one chain transfer agent is a cycloaliphatic or an aliphatic thiol having from 2 to 24 carbon atoms,
optionally at least one cyclic monomer having an exo-methylene group, and at least one further monomer which is a charged, ionisable, hydrophilic, or hydrophobic monomer of the following formula (V):

$(CH_2=CR_{11})CO\text{-M-F}$ (V)

wherein:
$R_{11}$ represents H or a $C_1$-$C_6$ alkyl;
M represents a single bond or a linker moiety having from 1 to 20 carbon atoms;
F represents a charged, ionisable, hydrophilic, or hydrophobic group having 100 atoms at the most;
wherein the optional at least one cyclic monomer having an exo-methylene group is one of formula (III):

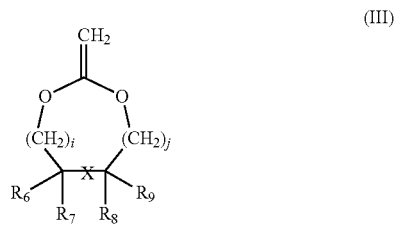

(III)

wherein:
$R_6$, $R_7$, $R_8$ and $R_9$ represent independently H or a $C_5$-$C_7$ aryl group or $R_6$ and $R_9$ are absent
and $R_7$ and $R_8$ form together with the carbon atom on which they are bonded a $C_5$-$C_7$ aryl group;
i and j represent independently an integer from 0 to 2; and X represents either O or X is not present and in this latter case, $CR_6R_7$ and $CR_8R_9$ are linked via a single bond C—C, and wherein the loaded macromolecule is selected from the group consisting of proteins and nucleic acids.

7. The polymer of claim 6, wherein F is selected from the group consisting of COOH, COOH, COO$^-$, $SO_3H$, $SO_3^-$, $PO_4H_2$, $PO_4H^-$, $PO_4^{2-}$, $NR_9R_{10}$, $NR_9R_{12}R_{10}^+$, $R_9$, $R_{12}$ and $R_{10}$ independently representing H or a $C_1$-$C_6$ alkyl, a $C_1$-$C_{20}$ alkyl group, a $C_5$-$C_{20}$ aryl group, a (5-30-members) heteroaryl group containing an heteroatom selected from the group consisting of O, N or S, a O—$C_5$-$C_{20}$ aryl group and a O-(5-30-members)heteroaryl group, a crown ether, and a cyclodextrin.

8. The polymer of claim 1, wherein the loaded macromolecule is selected from the group consisting of enzymes, antibodies, cytokines, growth factor, coagulation factors, hormones, plasmids, antisense oligonucleotides, siRNA, ribozymes, DNAzymes, aptamers, cationic polymers for nucleic acid loading, anti-inflammatory proteins, bone morphogentic proteins, angiogenic factors, vascular endothelial growth factors, TGF-beta, and inhibitors of angiogenesis.

9. The polymer of claim 1, which is in the form of a film, a foam, a particle, a lump, a thread, or a sponge.

10. A pharmaceutical composition comprising at least one macromolecule loaded bioresorbable crosslinked polymer of claim 1, in association with a pharmaceutically acceptable carrier.

11. An injectable pharmaceutical composition comprising
(a) a macromolecule-loaded bioresorbable crosslinked polymer obtainable as described in claim 1 having a spherical shape of a diameter of between 50 and 500 μm and a resorption time of between 2 days to 3 weeks;
(b) a macromolecule-loaded bioresorbable crosslinked polymer obtainable as described in claim 1 having a spherical shape of a diameter of between 50 and 500 μm and a resorption time of between one to 3 months; and
(c) at least a pharmaceutically acceptable excipients.

12. The composition of claim 11, wherein the spherical particles of macromolecule-loaded bioresorbable crosslinked polymers (a) and (b) do not have the same diameter.

13. An implant containing the macromolecule-loaded bioresorbable crosslinked polymer of claim 1.

14. The implant of claim 13, for implantation into tissues, brain, spinal cord, bones defects, internal anatomical spaces, body cavities, ducts and vessels.

15. The macromolecule-loaded bioresorbable crosslinked polymer of claim 1, wherein the at least one chain transfer agent is a cycloaliphatic or an aliphatic thiol having from 2 to 24 carbon atoms, and having a further functional group selected from the group consisting of amino, hydroxy and carboxy.

16. The polymer of claim 5 wherein the at least cyclic monomer of formula (III) is selected from the group consisting of 2-methylene-1,3-dioxepane, 5,6-benzo-2-methylene-1,3dioxepane and 2-methylene-1,3,6-trioxocane.

17. The polymer of claim 8 wherein the loaded macromolecule is selected from the group consisting of growth hormones, poly(allylamine hydrochloride), polydiallyldimethylammonium, polyethylenimine, poly(L-lysine), polydopamine, chitosan, polyamidoamine dendrimers, infliximab, rilonacept, fibroblast growth factors, bevacizumab and pegaptanib.

18. The composition of claim 12 wherein the diameter of the spherical particles of polymer (a) is of between 100 and 300 μm and the diameter of the spherical particles of polymer (b) is of between 300 and 500 μm.

* * * * *